US009340520B2

(12) United States Patent
Lopez et al.

(10) Patent No.: US 9,340,520 B2
(45) Date of Patent: May 17, 2016

(54) HEPATITIS C VIRUS INHIBITORS

(71) Applicant: Bristol-Myers Squibb Company, Princeton, NJ (US)

(72) Inventors: Omar D. Lopez, Wallingford, CT (US); John A. Bender, Middletown, CT (US); Makonen Belema, North Haven, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/017,837

(22) Filed: Sep. 4, 2013

(65) Prior Publication Data

US 2014/0012020 A1    Jan. 9, 2014

Related U.S. Application Data

(62) Division of application No. 13/361,541, filed on Jan. 30, 2012, now Pat. No. 8,552,047.

(60) Provisional application No. 61/467,602, filed on Mar. 25, 2011, provisional application No. 61/440,086, filed on Feb. 7, 2011.

(51) Int. Cl.
| | |
|---|---|
| C07D 309/06 | (2006.01) |
| C07D 405/14 | (2006.01) |
| A61K 45/06 | (2006.01) |
| A61K 31/4178 | (2006.01) |

(52) U.S. Cl.
CPC .......... *C07D 309/06* (2013.01); *A61K 31/4178* (2013.01); *A61K 45/06* (2013.01); *C07D 405/14* (2013.01)

(58) Field of Classification Search
None
See application file for complete search history.

(56) References Cited

U.S. PATENT DOCUMENTS

| | | | |
|---|---|---|---|
| 5,654,451 A | 8/1997 | Kari | |
| 7,745,636 B2 | 6/2010 | Bachand et al. | |
| 7,894,996 B2 | 2/2011 | Rice et al. | |
| 8,178,531 B2 | 5/2012 | Or et al. | |
| 8,288,562 B2 | 10/2012 | Bachand et al. | |
| 8,303,944 B2 | 11/2012 | Bachand et al. | |
| 8,492,553 B2 | 7/2013 | Bachand et al. | |
| 8,574,563 B2 | 11/2013 | Bachand et al. | |
| 2010/0158862 A1 | 6/2010 | Kim et al. | |
| 2011/0092415 A1 | 4/2011 | DeGoey et al. | |
| 2011/0206637 A1 | 8/2011 | Or et al. | |
| 2011/0237636 A1 | 9/2011 | Belema et al. | |
| 2011/0268697 A1 | 11/2011 | Kim et al. | |
| 2011/0269956 A1* | 11/2011 | Pack et al. | 544/82 |
| 2011/0274648 A1* | 11/2011 | Lavoie et al. | 424/85.2 |
| 2011/0281910 A1* | 11/2011 | Lavoie et al. | 514/316 |
| 2011/0286961 A1* | 11/2011 | Belema et al. | 424/85.2 |
| 2011/0294819 A1* | 12/2011 | Lopez et al. | 514/252.11 |
| 2012/0195857 A1* | 8/2012 | Belema et al. | 424/85.7 |
| 2013/0012540 A1 | 1/2013 | Lavoie et al. | |
| 2013/0085147 A1 | 4/2013 | Lopez et al. | |
| 2013/0115193 A1 | 5/2013 | Lavoie et al. | |
| 2013/0183269 A1 | 7/2013 | Hewawasam et al. | |
| 2013/0317213 A1* | 11/2013 | Pack et al. | 544/82 |

FOREIGN PATENT DOCUMENTS

| | | |
|---|---|---|
| WO | WO 94/15909 | 7/1994 |
| WO | WO 2004/005264 | 1/2004 |
| WO | WO 2006/022442 | 3/2006 |
| WO | WO 2006/093867 | 9/2006 |
| WO | WO 2006/133326 | 12/2006 |
| WO | WO 2007/031791 | 3/2007 |
| WO | WO 2007/058384 | 5/2007 |
| WO | WO 2007/076034 | 7/2007 |
| WO | WO 2007/077186 | 7/2007 |
| WO | WO 2007/081517 | 7/2007 |
| WO | WO 2007/138242 | 12/2007 |
| WO | WO 2008/021927 | 2/2008 |
| WO | WO 2008/021928 | 2/2008 |
| WO | WO 2008/021936 | 2/2008 |
| WO | WO 2008/070447 | 6/2008 |
| WO | WO 2008/133753 | 11/2008 |
| WO | WO 2008/144380 | 11/2008 |
| WO | WO 2009/020825 | 2/2009 |
| WO | WO 2009/020828 | 2/2009 |
| WO | WO 2009/102568 | 8/2009 |
| WO | WO 2009/102633 | 8/2009 |
| WO | WO 2009/102694 | 8/2009 |
| WO | WO 2010/017401 | 2/2010 |
| WO | WO 2010/039793 | 4/2010 |
| WO | WO 2010/062821 | 6/2010 |
| WO | WO 2010/065668 | 6/2010 |
| WO | WO 2010/065674 | 6/2010 |
| WO | WO 2010/065681 | 6/2010 |
| WO | WO 2010/075376 | 7/2010 |
| WO | WO 2010/091413 | 8/2010 |
| WO | WO 2010/094977 | 8/2010 |
| WO | WO 2010/096302 | 8/2010 |
| WO | WO 2010/096462 | 8/2010 |
| WO | WO 2010/096777 | 8/2010 |

(Continued)

OTHER PUBLICATIONS

Fridell, R.A. et al., "Resistance Analysis of the Hepatitis C Virus NS5A Inhibitor BMS-790052 in an in Vitro Replicon System", Antimicrobial Agents and Chemotherapy, vol. 54, No. 9, pp. 3641-3650 (2010).

Gao, M. et al., "Chemical genetics strategy identifies an HCV NS5A inhibitor with a potent clinical effect", Nature, vol. 465, pp. 96-100 (2010).

Lemm, J.A. et al., "Identification of Hepatitis C Virus NS5A Inhibitors", Journal of Virology, vol. 84, No. 1, pp. 482-491 (2010).

Romine, J.L. et al., "Inhibitors of HCV NS5A: From Iminothiazolidinones to Symmetrical Stilbenes", ACS Medicinal Chemistry Letters, vol. 2, pp. 224-229 (2011).

*Primary Examiner* — Leslie A. Royds Draper
(74) *Attorney, Agent, or Firm* — Pamela A. Mingo

(57) ABSTRACT

The present disclosure relates to compounds, compositions and methods for the treatment of hepatitis C virus (HCV) infection. Also disclosed are pharmaceutical compositions containing such compounds and methods for using these compounds in the treatment of HCV infection.

1 Claim, No Drawings

(56) References Cited

FOREIGN PATENT DOCUMENTS

| | | |
|---|---|---|
| WO | WO 2010/099527 | 9/2010 |
| WO | WO 2010/111483 | 9/2010 |
| WO | WO 2010/111534 | 9/2010 |
| WO | WO 2010/111673 | 9/2010 |
| WO | WO 2010/117635 | 10/2010 |
| WO | WO 2010/117704 | 10/2010 |
| WO | WO 2010/117977 | 10/2010 |
| WO | WO 2010/120621 | 10/2010 |
| WO | WO 2010/120935 | 10/2010 |
| WO | WO 2010/122162 | 10/2010 |
| WO | WO 2010/132538 | 11/2010 |
| WO | WO 2010/132601 | 11/2010 |
| WO | WO 2010/138368 | 12/2010 |
| WO | WO 2010/138488 | 12/2010 |
| WO | WO 2010/138790 | 12/2010 |
| WO | WO 2010/138791 | 12/2010 |
| WO | WO 2010/144646 | 12/2010 |
| WO | WO 2010/148006 | 12/2010 |
| WO | WO 2011/004276 | 1/2011 |
| WO | WO 2011/009084 | 1/2011 |
| WO | WO 2011/015657 | 2/2011 |
| WO | WO 2011/015658 | 2/2011 |
| WO | WO 2011/026920 | 3/2011 |
| WO | WO 2011/028596 | 3/2011 |
| WO | WO 2011/031904 | 3/2011 |
| WO | WO 2011/031934 | 3/2011 |
| WO | WO 2011/046811 | 4/2011 |
| WO | WO 2011/050146 | 4/2011 |
| WO | WO 2011/054834 | 5/2011 |
| WO | WO 2011/059850 | 5/2011 |
| WO | WO 2011/059887 | 5/2011 |
| WO | WO 2011/060000 | 5/2011 |
| WO | WO 2011/066241 | 6/2011 |
| WO | WO 2011/068941 | 6/2011 |
| WO | WO 2011/075439 | 6/2011 |
| WO | WO 2011/075607 | 6/2011 |
| WO | WO 2011/075615 | 6/2011 |
| WO | WO 2011/079327 | 6/2011 |
| WO | WO 2011/081918 | 7/2011 |
| WO | WO 2011/082077 | 7/2011 |
| WO | WO 2011/087740 | 7/2011 |
| WO | WO 2011/091417 | 7/2011 |
| WO | WO 2011/091446 | 7/2011 |
| WO | WO 2011/091532 | 8/2011 |
| WO | WO 2011/109037 | 9/2011 |
| WO | WO 2011/112429 | 9/2011 |
| WO | WO 2011/119853 | 9/2011 |
| WO | WO 2011/119860 | 9/2011 |
| WO | WO 2011/119870 | 9/2011 |
| WO | WO 2011/127350 | 10/2011 |
| WO | WO 2011/146401 | 11/2011 |
| WO | WO 2011/149856 | 12/2011 |
| WO | WO 2011/150243 | 12/2011 |
| WO | WO 2011/153396 | 12/2011 |
| WO | WO 2011/154871 | 12/2011 |
| WO | WO 2011/156543 | 12/2011 |
| WO | WO 2011/156578 | 12/2011 |
| WO | WO 2012/003642 | 1/2012 |
| WO | WO 2012/013643 | 2/2012 |
| WO | WO 2012/018325 | 2/2012 |
| WO | WO 2012/018534 | 2/2012 |
| WO | WO 2012/018829 | 2/2012 |
| WO | WO 2012/020036 | 2/2012 |
| WO | WO 2012/021591 | 2/2012 |
| WO | WO 2012/021704 | 2/2012 |
| WO | WO 2012/027712 | 3/2012 |
| WO | WO 2012/040389 | 3/2012 |
| WO | WO 2012/040923 | 4/2012 |
| WO | WO 2012/040924 | 4/2012 |
| WO | WO 2012/041014 | 4/2012 |
| WO | WO 2012/041227 | 4/2012 |
| WO | WO 2012/048421 | 4/2012 |
| WO | WO 2012/050848 | 4/2012 |
| WO | WO 2012/050850 | 4/2012 |
| WO | WO 2012/050918 | 4/2012 |
| WO | WO 2012/051361 | 4/2012 |
| WO | WO 2012/061552 | 5/2012 |
| WO | WO 2012/068234 | 5/2012 |
| WO | WO 2012/074437 | 6/2012 |
| WO | WO 2012/083043 | 6/2012 |
| WO | WO 2012/083048 | 6/2012 |
| WO | WO 2012/083053 | 6/2012 |
| WO | WO 2012/083058 | 6/2012 |
| WO | WO 2012/083059 | 6/2012 |
| WO | WO 2012/083061 | 6/2012 |
| WO | WO 2012/083164 | 6/2012 |
| WO | WO 2012/083170 | 6/2012 |
| WO | WO 2012/087976 | 6/2012 |
| WO | WO 2012/116257 | 8/2012 |
| WO | WO 2012/122716 | 9/2012 |
| WO | WO 2012/123298 | 9/2012 |
| WO | WO 2012/125926 | 9/2012 |
| WO | WO 2012/135581 | 10/2012 |
| WO | WO 2012/154777 | 11/2012 |
| WO | WO 2012/162578 | 11/2012 |
| WO | WO 2012/162580 | 11/2012 |
| WO | WO 2012/166716 | 12/2012 |
| WO | WO 2012/175581 | 12/2012 |
| WO | WO 2013/007106 | 1/2013 |

* cited by examiner

HEPATITIS C VIRUS INHIBITORS

CROSS-REFERENCE TO RELATED APPLICATIONS

This Divisional application claims the benefit of U.S. Ser. No. 13/361,541 filed Jan. 30, 2012, now allowed, which in turn claims the benefit of U.S. Provisional Application Ser. No. 61/467,602 filed Mar. 25, 2011 and U.S. Provisional Application Ser. No. 61/440,086 filed Feb. 7, 2011.

The present disclosure is generally directed to antiviral compounds, and more specifically directed to compounds which can inhibit the function of the NS5A protein encoded by Hepatitis C virus (HCV), compositions comprising such compounds, and methods for inhibiting the function of the NS5A protein.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

The current standard of care for HCV, which employs a combination of pegylated-interferon and ribavirin, has a non-optimal success rate in achieving sustained viral response and causes numerous side effects. Thus, there is a clear and long-felt need to develop effective therapies to address this undermet medical need.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome due to the high error rate of the encoded RNA dependent RNA polymerase which lacks a proof-reading capability. At least six major genotypes have been characterized, and more than 50 subtypes have been described with distribution worldwide. The clinical significance of the genetic heterogeneity of HCV has demonstrated a propensity for mutations to arise during monotherapy treatment, thus additional treatment options for use are desired. The possible modulator effect of genotypes on pathogenesis and therapy remains elusive.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions by both acting as a cofactor for the NS3 protease and assisting in the membrane localization of NS3 and other viral replicase components. The formation of a NS3-NS4A complex is necessary for proper protease activity resulting in increased proteolytic efficiency of the cleavage events. The NS3 protein also exhibits nucleoside triphosphatase and RNA helicase activities. NS5B (also referred to herein as HCV polymerase) is a RNA-dependent RNA polymerase that is involved in the replication of HCV genome with other HCV proteins, including NS5A, in a replicase complex.

Compounds useful for treating HCV-infected patients are desired which selectively inhibit HCV viral replication. In particular, compounds which are effective to inhibit the function of the NS5A protein are desired. The HCV NS5A protein is described, for example, in the following references: S. L. Tan, et al., *Virology*, 284:1-12 (2001); K.-J. Park, et al., *J. Biol. Chem.*, 30711-30718 (2003); T. L. Tellinghuisen, et al., *Nature*, 435, 374 (2005); R. A. Love, et al., *J. Virol*, 83, 4395 (2009); N. Appel, et al., *J. Biol. Chem.*, 281, 9833 (2006); L. Huang, *J. Biol. Chem.*, 280, 36417 (2005); C. Rice, et al., WO2006093867.

Bachand, et. al. in WO2008/021927, published Feb. 21, 2008, disclose a series of biphenyl compounds which are useful for the treatment of Hepatitis C virus. The novel compounds of the present disclosure fall within the definition of the Formula in WO2008/021927 and are not disclosed or described by Bachand, et al. Surprisingly, it has been discovered that these compounds possess unique attributes which make them useful for the treatment of Hepatitis C virus.

In a first aspect the present disclosure provides a compound of Formula (I)

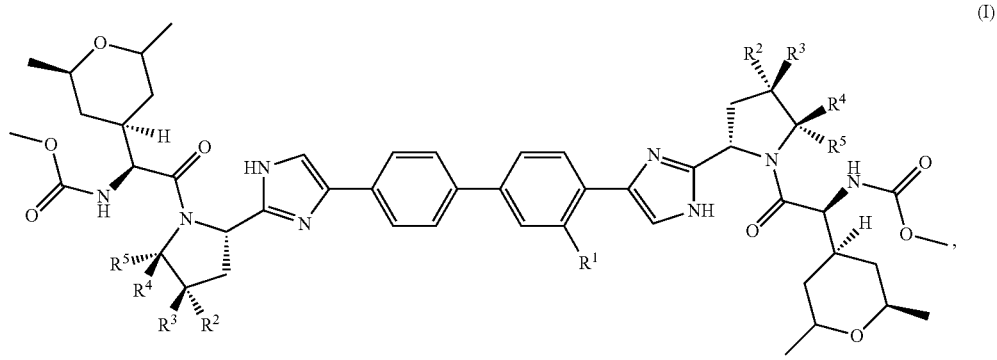

or a pharmaceutically acceptable salt thereof, wherein
R¹ is selected from hydrogen, methyl, and fluoro;
R² is selected from hydrogen and methyl;
R³ and R⁴ are each hydrogen; or
R³ and R⁴, together with the carbon atoms to which they are attached, form a cyclopropyl ring; and
R⁵ is selected from hydrogen and methyl.

In a first embodiment of the first aspect the present disclosure provides a compound of Formula (I), or a pharmaceutically acceptable salt thereof, wherein R¹ is hydrogen.

In a second embodiment of the first aspect the present disclosure provides a compound of Formula (I), or a pharmaceutically acceptable salt thereof, wherein R¹ is fluoro. In a third embodiment, R², R³, and R⁴ are each hydrogen and R⁵ is methyl.

In a fourth embodiment of the first aspect the present disclosure provides a compound of Formula (I), or a pharmaceutically acceptable salt thereof, wherein R¹ is methyl. In a fifth embodiment R², R³, and R⁴ are each hydrogen and R⁵ is methyl.

In a second aspect the present disclosure provides a compound selected from

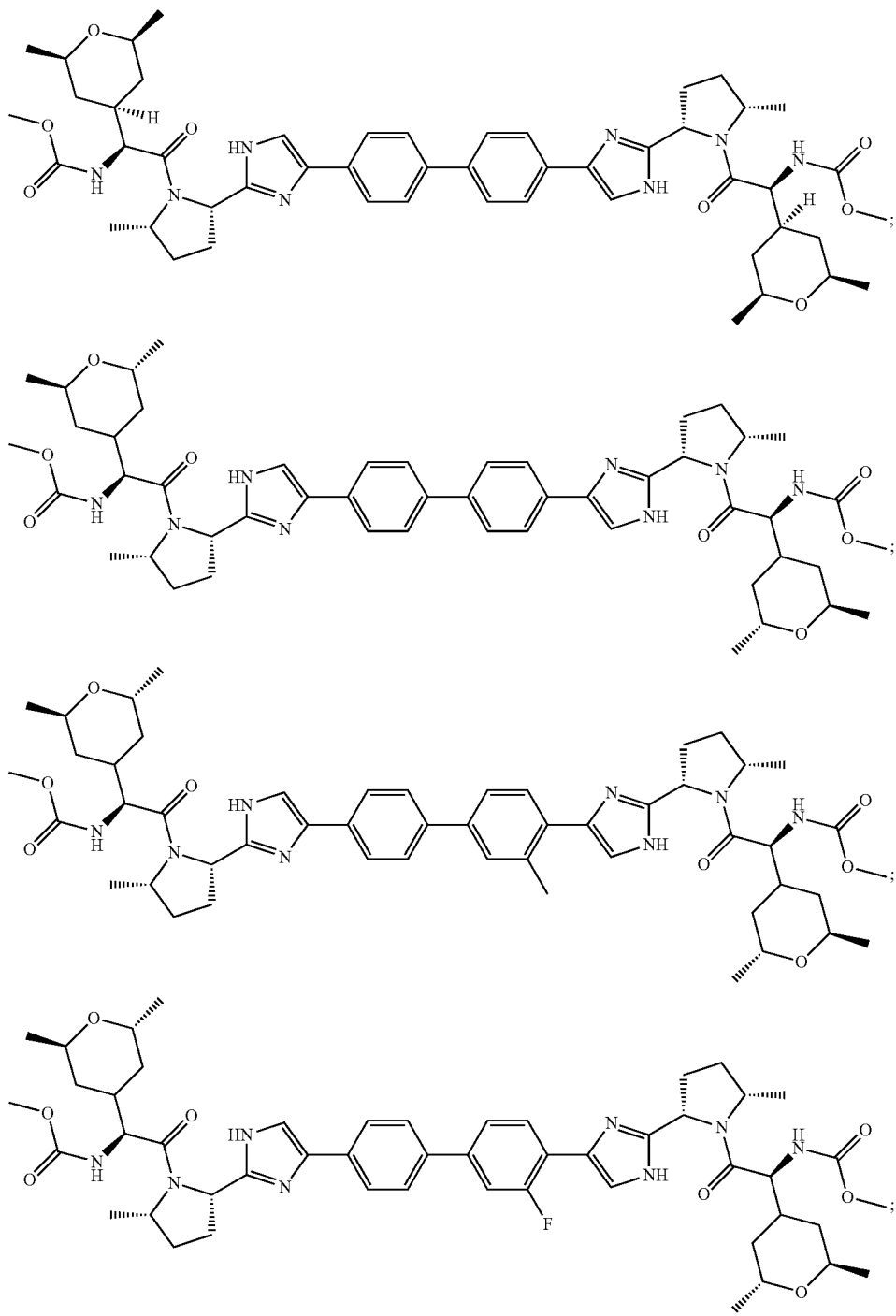

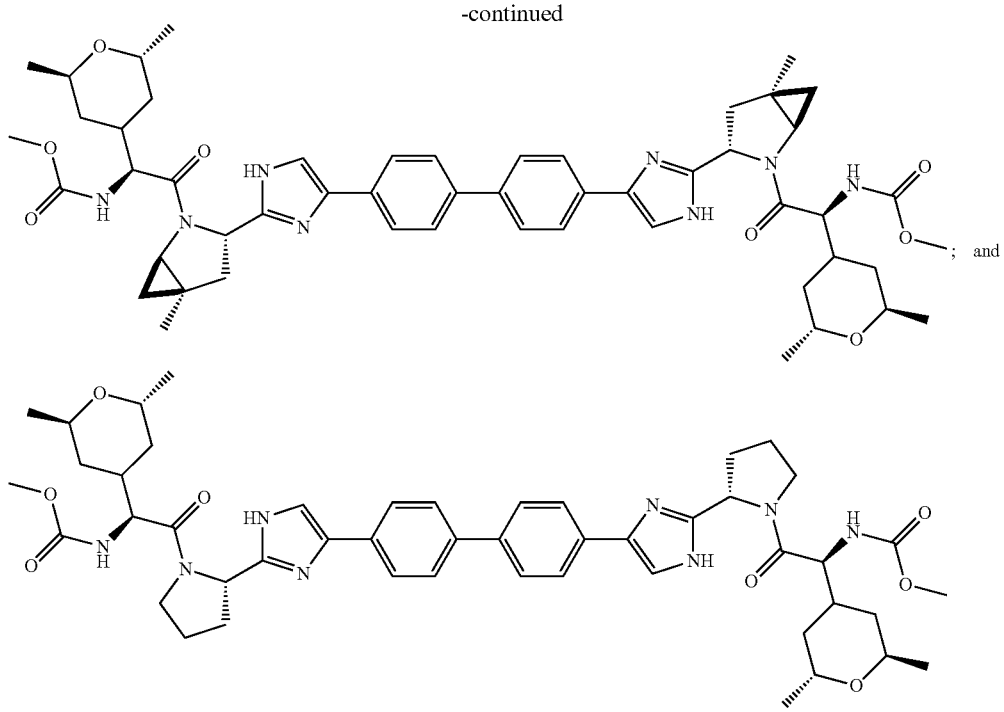

or a pharmaceutically acceptable salt thereof.

In a third aspect the present disclosure provides a composition comprising a compound of Formula (I), or a pharmaceutically acceptable salt thereof, and a pharmaceutically acceptable carrier. In a first embodiment of the third aspect the composition further comprises one, two, or three additional compounds having anti-HCV activity. In a second embodiment of the third aspect at least one of the additional compounds is an interferon or a ribavirin. In a third embodiment the interferon is selected from interferon alpha 2B, pegylated interferon alpha, consensus interferon, interferon alpha 2A, interferon lambda, and lymphoblastiod interferon tau.

In a fourth embodiment of the third aspect the present disclosure provides a composition comprising a compound of Formula (I), or a pharmaceutically acceptable salt thereof, a pharmaceutically acceptable carrier, and one or two additional compounds having anti-HCV activity, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

In a fifth embodiment of the third aspect the present disclosure provides a composition comprising a compound of Formula (I), or a pharmaceutically acceptable salt thereof, a pharmaceutically acceptable carrier, and one or two additional compounds having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a fourth aspect the present disclosure provides a method of treating an HCV infection in a patient, comprising administering to the patient a therapeutically effective amount of a compound of Formula (I), or a pharmaceutically acceptable salt thereof. In a first embodiment of the fourth aspect the method further comprises administering one, two, or three additional compounds having anti-HCV activity prior to, after or simultaneously with the compound of Formula (I), or a pharmaceutically acceptable salt thereof. In a second embodiment of the fourth aspect at least one of the additional compounds is an interferon or a ribavirin. In a third embodiment of the fourth aspect the interferon is selected from interferon alpha 2B, pegylated interferon alpha, consensus interferon, interferon alpha 2A, interferon lambda, and lymphoblastiod interferon tau.

In a fourth embodiment of the fourth aspect the present disclosure provides a method of treating an HCV infection in a patient, comprising administering to the patient a therapeutically effective amount of a compound of Formula (I), or a pharmaceutically acceptable salt thereof, and one or two additional compounds having anti-HCV activity prior to, after or simultaneously with the compound of Formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the fourth aspect the present disclosure provides a method of treating an HCV infection in a patient, comprising administering to the patient a therapeutically effective amount of a compound of Formula (I), or a pharmaceutically acceptable salt thereof, and one or two additional compounds having anti-HCV activity prior to, after or simultaneously with the compound of Formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In another aspect the present disclosure provides a compound which is

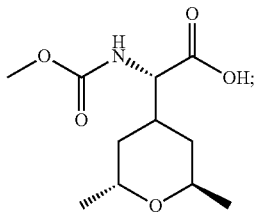 [SMILES: COC(=O)N[C@H](C(=O)O)C1C[C@@H](C)O[C@H](C)C1]

or a pharmaceutically acceptable salt thereof.

In another aspect the present disclosure provides a compound which is

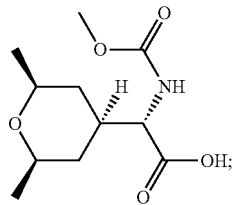 [SMILES: COC(=O)N[C@H](C(=O)O)[C@H]1C[C@@H](C)O[C@@H](C)C1]

or a pharmaceutically acceptable salt thereof.

Other embodiments of the present disclosure may comprise suitable combinations of two or more of embodiments and/or aspects disclosed herein.

Yet other embodiments and aspects of the disclosure will be apparent according to the description provided below.

The compounds of the present disclosure also exist as tautomers; therefore the present disclosure also encompasses all tautomeric forms.

The description of the present disclosure herein should be construed in congruity with the laws and principals of chemical bonding.

It should be understood that the compounds encompassed by the present disclosure are those that are suitably stable for use as pharmaceutical agent.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to inhibit NS5A. Individual stereoisomers of compounds can be prepared synthetically from commercially available starting materials which contain chiral centers or by preparation of mixtures of steroisomeric products followed by separation such as conversion to a mixture of diastereomers followed by separation or recrystallization, chromatographic techniques, or direct separation on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of Formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, dihydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by pulverizing the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, bentonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

The compounds of the present disclosure can also be administered with a cyclosporin, for example, cyclosporin A or other analogs working through similar mechanism. Cyclosporin A has been shown to be active against HCV in clinical trials (*Hepatology* 2003, 38, 1282; *Biochem. Biophys. Res. Commun.* 2004, 313, 42; *J. Gastroenterol.* 2003, 38, 567).

Table 1 below lists some illustrative examples of compounds that can be administered with the compounds of this disclosure. The compounds of the disclosure can be administered with other anti-HCV active compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |

TABLE 1-continued

| Brand Name | Physiological Class | Type of Inhibitor or Target | Source Company |
|---|---|---|---|
| ISIS 14803 | Antiviral | antisense | ISIS Pharmaceuticals Inc, Carlsbad, CA/Elan Phameuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |

TABLE 1-continued

| Brand Name | Physiological Class | Type of Inhibitor or Target | Source Company |
|---|---|---|---|
| Civacir | Immunosuppressant | HCV IgG immuno-suppressant | Nabi Biopharmaceuticals Inc., Boca Raton, FL |
| Albuferon - α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |

TABLE 1-continued

| Brand Name | Physiological Class | Type of Inhibitor or Target | Source Company |
|---|---|---|---|
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/ Bristol-Myers Squibb |
| INX-189 | Antiviral | Nucleotide NS5B Polymerase Inhibitor | Inhibitex |

The compounds of the present disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The abbreviations used in the present application, including particularly in the examples which follow, are well-known to those skilled in the art. Some of the abbreviations used are as follows: h, hr, or hrs for hours; EtOAc for ethyl acetate; Hex for hexanes; DCM for dichloromethane; DEAD for diethyl azodicarboxylate; Ph$_3$P for triphenylphosphine; Et$_2$O for diethyl ether; THF for tetrahydrofuran; LiHMDS for lithium hexamethyldisilazide; Ph for phenyl; DIEA or DIPEA or iPr$_2$EtN for diiosopropylethylamine; EtOH for ethanol; MeOH for methanol; DMSO for dimethylsulfoxide; RT or Rt or rt or R$_t$ for room temperature or retention time (context will dictate); ON or o/n for overnight; min for minutes; DCM for dichloromethane; HATU for O-(7-azabenzotriazol-1-yl)-N,N,N',N'-tetramethyluronium hexafluorophosphate; DMF for N,N-dimethylformamide; TFA for trifluoroacetic acid; HOBt or HOBT for hydroxybenzotriazole; DME for 1,2-dimethoxyethane; and DMAP for N,N-dimethylaminopyridine.

Cap-1

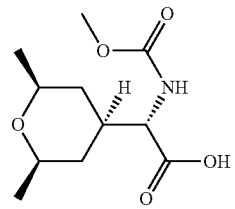 [SMILES: COC(=O)N[C@H](C(=O)O)[C@H]1C[C@@H](C)O[C@@H](C)C1]

Cap-1

Step a

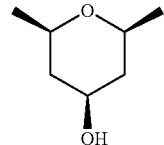

2,6-Dimethyl-4H-pyran-4-one (15 g, 121 mmol) was dissolved in ethanol (300 mL) and 10% Pd/C (1.28 g, 1.21 mmol) was added. The mixture was hydrogenated in a Parr shaker under H$_2$ (70 psi) at room temperature for 72 hrs. The reaction mixture was filtered through a pad of diatomaceous earth (Celite®) and washed with ethanol. The filtrate was concentrated in vacuum and the residue was purified via flash chromatography (10% to 30% EtOAc/Hex). Two fractions of clear oils were isolated. The first eluting fractions were a mixture of (2R,4r,6S)-2,6-dimethyltetrahydro-2H-pyran-4-ol (Cap-1, step a) and (2R,4s,6S)-2,6-dimethyltetrahydro-2H-pyran-4-ol (1.2 g) while the latter eluting fractions corresponded to only Cap-1, step a (10.73 g). $^1$H NMR (500 MHz, CDCl$_3$) δ ppm 3.69-3.78 (1H, m), 3.36-3.47 (2H, m), 2.10 (1H, br. s.), 1.88 (2H, dd, J=12.05, 4.73 Hz), 1.19 (6H, d, J=6.10 Hz), 1.10 (2H, q, J=10.70 Hz). $^{13}$C NMR (126 MHz, CDCl$_3$) δ ppm 71.44 (2C), 67.92 (1C), 42.59 (2C), 21.71 (2C).

Cap-1

Step b

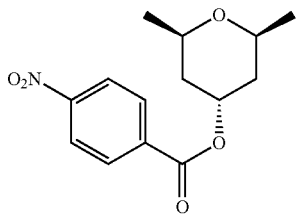 [SMILES: C[C@@H]1C[C@@H](OC(=O)c2ccc([N+](=O)[O-])cc2)C[C@H](C)O1]

DEAD (166 mL, 330 mmol) was added drop wise to a solution of Cap-1, step a (10.73 g, 82 mmol), 4-nitrobenzoic acid (48.2 g, 288 mmol) and Ph$_3$P (86 g, 330 mmol) in benzene (750 mL). Heat evolution was detected and the resulting amber solution was stirred at ambient temperature for 18 h. Solvent was removed under reduced pressure and the residue was triturated with Et$_2$O (200 mL) to remove triphenylphosphine oxide (10 g). The remaining mixture was purified via Biotage® (0 to 5% EtOAc/Hex; 300 g column×4). A white solid corresponding to Cap-1, step b (19.36 g) was isolated. $^1$H NMR (500 MHz, CDCl$_3$) δ ppm 8.27-8.32 (2H, m), 8.20-8.24 (2H, m), 5.45 (1H, quin, J=2.82 Hz), 3.92 (2H, dqd, J=11.90, 6.10, 1.53 Hz), 1.91 (2H, dd, J=14.80, 2.29 Hz), 1.57 (2H, dt, J=14.65, 3.05 Hz), 1.22 (6H, d, J=6.10 Hz). $^{13}$C NMR (126 MHz, CDCl$_3$) δ ppm 163.81 (1C), 150.55 (1C), 135.94 (1C), 130.64 (2C), 123.58 (2C), 70.20 (1C), 68.45 (2C), 36.95 (2C), 21.84 (2C). LC-MS: Anal. Calcd. for [M]$^+$ C$_{14}$H$_{12}$NO$_5$: 279.11. Found 279.12.

Cap-1

Step c

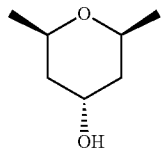

A solution of LiOH (8.30 g, 347 mmol) in water (300 mL) was added to a solution of Cap-1, step b (19.36 g, 69.3 mmol) in THF (1000 mL) and the resulting mixture was stirred at ambient temperature for 16 h. THF was removed under reduced pressure and the aqueous layer was diluted with more water (200 mL) and extracted with EtOAc (3×200 mL). The combined organic layers were dried (MgSO$_4$), filtered and concentrated under vacuum. An oily residue with a white solid was recovered. The mixture was triturated with hexanes and the solid was removed by filtration to yield a clear oil corresponding to Cap-1, step c (8.03 g). $^1$H NMR (500 MHz, CDCl$_3$) δ ppm 4.21 (1H, quin, J=2.82 Hz), 3.87-3.95 (2H, m), 1.72 (1H, br. s.), 1.63 (2H, dd, J=14.34, 2.14 Hz), 1.39-1.47 (2H, m), 1.17 (6H, d, J=6.41 Hz). $^{13}$C NMR (126 MHz, CDCl$_3$) δ ppm 67.53 (2C), 64.71 (1C), 39.99 (2C), 21.82 (2C).

Cap-1

Step d

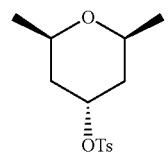

p-Tosyl chloride (23.52 g, 123 mmol) was added to a solution of Cap-1, step c (8.03 g, 61.7 mmol) and pyridine (19.96 mL, 247 mmol) in CH$_2$Cl$_2$ (750 mL) at room temperature and stirred for 36 h. As the reaction did not proceed to completion, CH$_2$Cl$_2$ was removed under reduced pressure and stirring continued for another 48 h. The mixture was then added to CH$_2$Cl$_2$ (100 mL) and water (100 mL) and stirred at ambient temperature for 2 h. The mixture was separated and the organic layer was the washed thoroughly with 1N aq. HCl (2×50 mL). The organic layer was then dried (MgSO$_4$), filtered and concentrated. A yellow oil corresponding to Cap-1, step d (14.15 g) was isolated, which solidified under vacuum as an off-white solid. $^1$H NMR (500 MHz, CDCl$_3$) δ ppm 7.80 (2H, d, J=8.24 Hz), 7.35 (2H, d, J=7.93 Hz), 4.88 (1H, quin, J=2.82 Hz), 3.79-3.87 (2H, m), 2.46 (3H, s), 1.76 (2H, dd, J=14.50, 2.59 Hz), 1.36 (2H, ddd, J=14.34, 11.60, 2.75 Hz), 1.12 (6H, d, J=6.10 Hz). $^{13}$C NMR (126 MHz, CDCl$_3$) δ ppm 144.64 (1C), 134.24 (1C), 129.82 (2C), 127.61 (2C), 77.34 (1C), 67.68 (2C), 37.45 (2C), 21.61 (1C), 21.57 (2C). LC-MS: Anal. Calcd. for [2M+H]$^+$ C$_{28}$H$_{41}$O$_8$S$_2$: 569.22. Found 569.3.

Cap-1

Step e

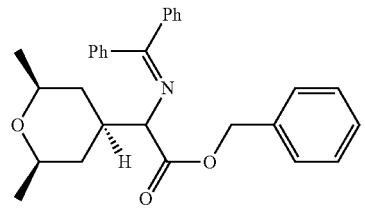 [SMILES: C[C@@H]1C[C@H](C(N=C(c2ccccc2)c2ccccc2)C(=O)OCc2ccccc2)C[C@H](C)O1]

LiHMDS (29.7 mL, 29.7 mmol, 1 M in THF) was added to a solution of Cap-1, step d (7.05 g, 24.8 mmol) and benzyl 2-(diphenylmethyleneamino)acetate (8.57 g, 26.0 mmol) in toluene (80 mL) at room temperature in a pressure tube and the resulting mixture was then stirred for 5 h at 100° C. The reaction was quenched with water (100 mL), extracted with EtOAc, washed with water, dried over MgSO$_4$, filtrated, and concentrated in vacuum. The residue was purified via Biotage® (0% to 15% EtOAc/Hex; 240 g column) and a yellow oil corresponding to Cap-1, step e (8.76 g) was isolated as a racemic mixture. $^1$H NMR (400 MHz, CDCl$_3$) δ ppm 7.62-7.71 (2H, m), 7.30-7.45 (11H, m), 7.05 (2H, dd, J=7.65, 1.63 Hz), 5.13-5.22 (2H, m), 3.89 (1H, d, J=6.78 Hz), 3.46 (2H, dquind, J=11.27, 5.90, 2.01 Hz), 2.34-2.45 (1H, m), 1.58-1.66 (1H, m), 1.34-1.43 (1H, m), 1.19 (3H, d, J=6.02 Hz), 1.03-1.16 (4H, m), 0.83-0.97 (1H, m). $^{13}$C NMR (101 MHz, CDCl$_3$) δ ppm 170.84 (1C), 170.68 (1C), 139.01 (1C), 135.96 (1C), 135.51 (1C), 130.04 (1C), 128.49 (2C), 128.20 (1C), 128.09 (4C), 127.97 (2C), 127.85 (1C), 127.67 (2C), 127.47 (2C), 72.76 (1C), 72.46 (1C), 69.77 (1C), 65.99 (1C), 39.11 (1C), 35.90 (1C), 35.01 (1C), 21.74 (1C), 21.65 (1C). LC-MS Anal. Calcd. for [2M+Na]$^+$ C$_{58}$H$_{62}$N$_2$NaO$_6$: 905.45. Found 905.42.

Cap-1

Step f

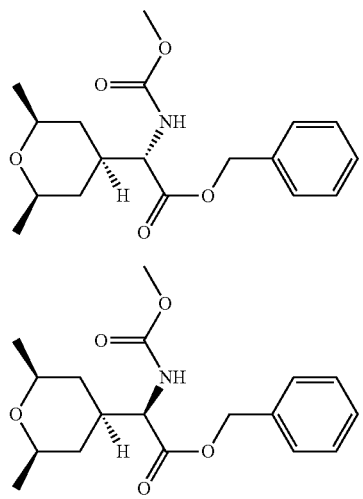

Cap-1, step f.1

Cap-1, step f.2

Cap-1, step e (8.76 g, 19.84 mmol) was dissolved in THF (100 mL) and treated with 2 N HCl in water (49.6 mL, 99 mmol). The resulting clear solution was stirred at ambient temperature for 4 h and then THF was removed under reduced pressure. The remaining aqueous layer was extracted with EtOAc (3×30 mL) and concentrated under vacuum, to afford the corresponding crude amine. The residue was taken up in CH$_2$Cl$_2$ (100 mL) and charged with DIEA (11.8 mL, 67.6 mmol) and methyl chloroformate (1.962 mL, 25.3 mmol). The resulting solution was stirred at ambient temperature for 2 h. The reaction mixture was diluted with CH$_2$Cl$_2$ (50 mL) and washed with water (100 mL) and brine (100 mL). The organic layer was dried (MgSO$_4$), filtered and concentrated. The residue was purified via Biotage® (15% to 25% EtOAc/Hex; 80 g column). A clear colorless oil corresponding to racemic Cap-1, step f (5.27 g) was recovered. $^1$H NMR (400 MHz, CDCl$_3$) δ ppm 7.32-7.41 (5H, m), 5.13-5.28 (3H, m), 4.36 (1H, dd, J=8.16, 4.64 Hz), 3.69 (3H, s), 3.30-3.47 (2H, m), 2.00-2.16 (1H, m), 1.52 (1H, d, J=12.55 Hz), 1.33 (1H, d, J=12.30 Hz), 1.15 (6H, dd, J=6.02, 5.02 Hz), 0.88-1.07 (2H, m). $^{13}$C NMR (101 MHz, CDCl$_3$) δ ppm 171.39 (1C), 156.72 (1C), 135.20 (2C), 128.60 (2C), 128.57 (1C), 128.52 (2C), 72.77 (1C), 72.74 (1C), 67.16 (1C), 57.81 (1C), 52.40 (1C), 38.85 (1C), 35.56 (1C), 34.25 (1C), 21.94 (2C). LC-MS: Anal. Calcd. for [M+H]$^+$ C$_{18}$H$_{26}$NO$_5$: 336.18. Found 336.3.

A chiral method was developed to separate the racemic mixture by using 20% ethanol as the modifier on a CHIRAL-PAK® AS-H column (50×500 mm, 20 μm) (Wavelength=220 nm, Flow rate=100 mL/min for 22 min, Solvent A=0.1% diethylamine in heptanes, Solvent B=EtOH). The two separated isomers, corresponded to (S)-benzyl 2-((2R,4r,6S)-2,6-dimethyltetrahydro-2H-pyran-4-yl)-2-((methoxycarbonyl)amino)acetate (Cap-1, step E 1) (Rt=9.8 min, 2.2 g) and (R)-benzyl 2-((2R,4r,6S)-2,6-dimethyltetrahydro-2H-pyran-4-yl)-2-((methoxycarbonyl)amino)acetate (Cap-1, step f.2) (Rt=16.4 min, 2.1 g) and they each exhibited the same analytical data as the corresponding mixture (see above).

Cap-1

(S)-benzyl 2-((2R,4r,6S)-2,6-dimethyltetrahydro-2H-pyran-4-yl)-2-((methoxycarbonyl)amino)acetate (Cap-1, step f.1) (2.2 g, 6.6 mmol) was dissolved in MeOH (50 mL) in a Parr bottle and charged with 10% Pd/C (0.349 g, 0.328 mmol). The suspension was then placed in a Parr shaker and the mixture was flushed with N$_2$ (3×), placed under 40 psi of H$_2$ and shaken at room temperature for 15 h. The catalyst was filtered off through a pad of diatomaceous earth (Celite®) and the solvent was removed under reduced pressure, to yield an amber solid corresponding to Cap-1 (1.6 g). $^1$H NMR (500 MHz, DMSO-d$_6$) δ ppm 12.74 (1H, br. s.), 7.35 (1H, d, J=6.10 Hz), 3.85 (1H, br. s.), 3.53 (3H, s), 3.35 (2H, ddd, J=15.95, 9.99, 6.10 Hz), 1.97 (1H, br. s.), 1.48 (2H, t, J=13.28 Hz), 1.06 (6H, d, J=6.10 Hz), 0.82-1.00 (2H, m). $^{13}$C NMR (101 MHz, DMSO-d$_6$) δ ppm 176.93 (1C), 156.72 (1C), 72.10 (1C), 71.92 (1C), 58.54 (1C), 51.35 (1C), 36.88 (1C), 35.82 (1C), 34.71 (1C), 21.90 (2C). Note: The absolute stereochemistry of Cap-1 was determined by single crystal X-ray analysis of an ester analog prepared from Cap-1 and (S)-phenethanol.

Cap-2

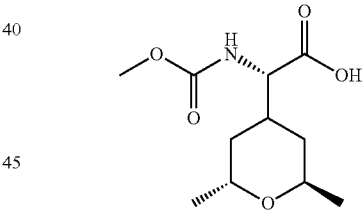

(S)-2-((2R,6R)-2,6-dimethyltetrahydro-2H-pyran-4-yl)-2-(methoxycarbonylamino)acetic acid Cap-2

Step a

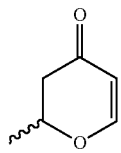

Reference: S. Danishefsky; et al. *J. Org. Chem*, 1982, 47, 1597.

Boron trifluoride etherate (3.81 mL, 30.5 mmol) was added dropwise to a stirred and cooled (−78° C.) solution of (E)-(4-methoxybuta-1,3-dien-2-yloxy)trimethylsilane (5.0 g, 29 mmol) and acetaldehyde (3.28 mL, 58.0 mmol) in diethyl ether (100 mL) under nitrogen. The reaction was stirred at −78° C. for 2.5 h and then quenched with sat. aq. NaHCO$_3$ (40 mL), allowed to warm to RT and stirred ON. The layers were separated and the aqueous layer was extracted with diethyl ether (2×50 mL). The combined organic layers were dried (MgSO$_4$), filtered and concentrated to a yellow/orange oil. The crude oil was purified with a Biotage® Horizon (110 g SiO$_2$, 25-40% EtOAc/hexanes) to yield racemic 2-methyl-2H-pyran-4(3H)-one (Cap-2, step a) (2.2 g) as a yellow oil. $^1$H NMR (400 MHz, CDCl$_3$-d) δ ppm 7.35 (d, J=6.0 Hz, 1H), 5.41 (dd, J=6.0, 1.0 Hz, 1H), 4.51-4.62 (m, 1H), 2.41-2.57 (m, 2H), 1.47 (d, J=6.3 Hz, 3H).

Cap-2

Step b

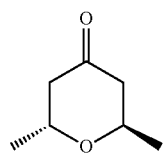

Reference: Reddy, D. S.; et al. *J. Org. Chem.* 2004, 69, 1716-1719.

A solution of 1.6M methyllithium in diethyl ether (20.9 mL, 33.4 mmol) was added to a stirred slurry of copper(I) iodide (4.25 g, 22.30 mmol) in diethyl ether (30 mL) at 0° C. and under nitrogen. The reaction was stirred at 0° C. for 20 min and then racemic 2-methyl-2H-pyran-4(3H)-one (1.25 g, 11.2 mmol) in diethyl ether (12.0 mL) was added over 10 min. The reaction was allowed to warm to RT and stirred 2 h. The reaction mixture was poured into sat NH$_4$Cl (aq) and stirred 20 min. The solution was extracted with diethyl ether (4×60 mL) and the combined organics were washed with brine (~80 mL), dried (MgSO$_4$), filtered and concentrated to yield racemic (2R,6R)-2,6-dimethyldihydro-2H-pyran-4(3H)-one (Cap-2, step b) (1.34 g) as an orange oil. $^1$H NMR (400 MHz, CDCl$_3$) δ ppm 4.28-4.39 (m, 2H), 2.55 (ddd, J=14.1, 4.8, 1.5 Hz, 2H), 2.24 (ddd, J=14.1, 6.5, 1.5 Hz, 2H), 1.28 (d, J=6.3 Hz, 6H).

Cap-2

Step c

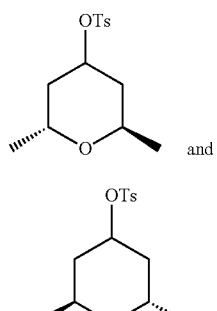

Sodium borohydride (0.354 g, 9.36 mmol) was added in portions to a stirred solution of racemic (2R,6R)-2,6-dimethyldihydro-2H-pyran-4(3H)-one (Cap-2, step b) (1.2 g, 9.4 mmol) in MeOH (30 mL) at 0° C. The solution was stirred 10 min at 0° C., warmed to RT and stirred 1 h. The reaction was poured into sat NH$_4$Cl (~50 mL), stirred 20 min and then partially concentrated (to ~½ volume). A precipitate formed, water was added until homogeneous and then the solution was extracted with DCM (3×60 mL). The aqueous layer was acidified with 1N HCl and then extracted with DCM (3×60 mL). The combined organics were dried with Na$_2$SO$_4$, filtered and concentrated to form a cloudy yellow oil (1.08 g). The crude oil was dissolved into DCM (8.0 mL) and then p-tosyl-Cl (2.68 g, 14.0 mmol) and pyridine (1.51 mL, 18.7 mmol) were added and the reaction was allowed to stir at RT for 2.5 d. The reaction was diluted with sat NH$_4$Cl (~60 mL) and extracted with DCM (3×30 mL). The combined organic phase was dried (MgSO$_4$), filtered and concentrated to a brown oil. The oil was purified on a Biotage® Horizon (80 g SiO$_2$, 10-25% EtOAc/hexanes) to yield racemic (2R,6R)-2,6-dimethyltetrahydro-2H-pyran-4-yl 4-methylbenzenesulfonate (Cap-2, step c) (1.63 g) as a viscous clear colorless oil. LC-MS retention time 3.321 min; m/z 284.98 [M+H]$^+$. LC data was recorded on a Shimadzu LC-10AS liquid chromatograph equipped with a Phenomenex-Luna 3u C18 2.0× 50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode. $^1$H NMR (400 MHz, CDCl$_3$) δ ppm 7.81 (d, J=8.3 Hz, 2H), 7.36 (d, J=8.0 Hz, 2H), 4.81-4.92 (m, 1H), 4.17-4.26 (m, 1H), 3.78-3.87 (m, 1H), 2.47 (s, 3H), 1.91-1.99 (m, 1H), 1.78-1.86 (m, 1H), 1.65-1.72 (m, 1H), 1.46 (ddd, J=12.9, 9.4, 9.3 Hz, 1H), 1.20 (dd, J=6.5, 4.8 Hz, 6H).

The racemic mixture was separated into the individual enantiomers in multiple injections using chiral preparative SFC purification (Chiralpak AD-H preparative column, 30×250 mm, 5 μm, 10% 1:1 EtOH/heptane in CO$_2$, 70 mL/min. for 10 min) to yield (2R,6R)-2,6-dimethyltetrahydro-2H-pyran-4-yl 4-methylbenzenesulfonate (Cap-2, step c.1) (577 mg) as the first eluting peak and (2S,6S)-2,6-dimethyltetrahydro-2H-pyran-4-yl 4-methylbenzenesulfonate (Cap-2, step c.2) (588 mg) as the second eluting peak. Each enantiomer was isolated as a clear colorless oil which solidified to a white solid upon standing.

Cap-2

Step d

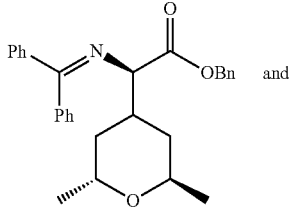

Cap-2, step d.2

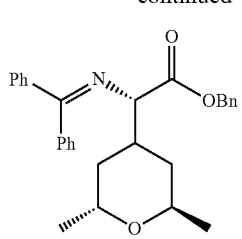

In a 48 mL pressure tube, (2R,6R)-2,6-dimethyltetrahydro-2H-pyran-4-yl 4-methylbenzenesulfonate (Cap-2, step c.1) (575 mg, 2.02 mmol) and benzyl 2-(diphenylmethyleneamino)acetate (733 mg, 2.22 mmol) were stirred in THF (2 mL) and toluene (10 mL). The clear colorless solution was flushed with nitrogen and then LiHMDS (1.0M in THF) (2.22 mL, 2.22 mmol) was added and the vessel was sealed and heated at 100° C. for 8 h. The reaction was cooled to RT, poured into ½ sat NH$_4$Cl (aq) (~50 mL) and extracted with EtOAc (3×30 mL). The combined organic layers were washed with brine, dried (MgSO$_4$), filtered and concentrated to a crude orange oil. The oil was purified on a Biotage® Horizon (40 g SiO$_2$, 10-25% EtOAc/hexanes) to yield impure desired product (501 mg) as an orange oil. This material was repurified on a Biotage® Horizon (25 g SiO$_2$, 6-12% EtOAc/hexanes) to yield an ~1:1 mixture of diastereomers (Cap-2, step d) (306 mg) as a viscous orange oil.

The mixture was separated into the individual diastereomers in multiple injections using chiral preparative SFC purification (Chiralcel OJ-H preparative column, 30×250 mm, 5 μm, 10% 1:1 EtOH/heptane in CO$_2$ @150 bar, 70 mL/min. for 10 min) to yield (R)-benzyl 2-((2R,6R)-2,6-dimethyltetrahydro-2H-pyran-4-yl)-2-(diphenylmethyleneamino)acetate (Cap-2, step d.1) (124 mg) as the first eluting peak and (S)-benzyl 2-((2R,6R)-2,6-dimethyltetrahydro-2H-pyran-4-yl)-2-(diphenylmethyleneamino)acetate (Cap-2, step d.2) (129 mg) as the second eluting peak. Each diastereomer was isolated as a viscous yellow oil.

Analytical data for (R)-benzyl 2-((2R,6R)-2,6-dimethyltetrahydro-2H-pyran-4-yl)-2-(diphenylmethyleneamino)acetate (Cap-2, step d.1): $^1$H NMR (400 MHz, D$_4$-MeOH) δ ppm 7.57-7.61 (m, 2H), 7.41-7.48 (m, 4H), 7.33-7.40 (m, 7H), 7.03-7.08 (m, 2H), 5.22 (d, J=12.1 Hz, 1H), 5.16 (d, J=12.1 Hz, 1H), 4.09-4.19 (m, 1H), 3.84 (d, J=6.8 Hz, 1H), 3.75-3.83 (m, 1H), 2.53-2.64 (m, 1H), 1.58-1.65 (m, 1H), 1.33-1.43 (m, 1H), 1.26-1.32 (m, 1H), 1.24 (d, J=7.0 Hz, 3H), 1.10 (d, J=6.0 Hz, 3H), 0.98-1.08 (m, 1H). LC-MS retention time 4.28 min; m/z 442.16 [M+H]$^+$. LC data was recorded on a Shimadzu LC-10AS liquid chromatograph equipped with a Phenomenex-Luna 3u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode.

Analytical data for (S)-benzyl 2-((2R,6R)-2,6-dimethyltetrahydro-2H-pyran-4-yl)-2-(diphenylmethyleneamino)acetate (Cap-2, step d.2): $^1$H NMR (400 MHz, D$_4$-MeOH) δ ppm 7.57-7.61 (m, 2H), 7.41-7.50 (m, 4H), 7.33-7.40 (m, 7H), 7.04-7.08 (m, 2H), 5.22 (d, J=12.1 Hz, 1H), 5.16 (d, J=12.1 Hz, 1H), 4.20 (qd, J=6.4, 6.3 Hz, 1H), 3.86 (d, J=6.5 Hz, 1H), 3.74-3.83 (m, 1H), 2.53-2.64 (m, 1H), 1.60 (td, J=12.7, 5.6 Hz, 1H), 1.38-1.51 (m, 2H), 1.26 (d, J=7.0 Hz, 3H), 1.04 (d, J=6.0 Hz, 3H), 0.79-0.89 (m, 1H). LC-MS retention time 4.27 min; m/z 442.17 [M+H]$^+$. LC data was recorded on a Shimadzu LC-10AS liquid chromatograph equipped with a Phenomenex-Luna 3u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode.

Cap-2

Step e

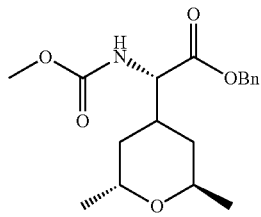 [SMILES: COC(=O)N[C@H](C(=O)OCc1ccccc1)C1C[C@@H](C)O[C@H](C)C1]

(S)-Benzyl 2-((2R,6R)-2,6-dimethyltetrahydro-2H-pyran-4-yl)-2-(diphenylmethyleneamino)acetate (Cap-2, step d.2) (129.6 mg, 0.294 mmol) was dissolved in THF (2 mL) and then treated with 2N HCl (1.0 mL, 2.1 mmol) in water. The reaction was stirred for 2 h and then concentrated under a stream of nitrogen overnight. The crude residue was dissolved in DCM (2 mL) and DIPEA (0.21 mL, 1.2 mmol) and then treated with methyl chloroformate (0.032 mL, 0.41 mmol) and stirred at RT for 4 h. The reaction was diluted with water (~2.5 mL) and extracted with DCM (4×2 mL). The combined organic phase was concentrated under a stream of nitrogen overnight and the residue was purified with a Biotage® Horizon (4 g SiO$_2$, 10-50% EtOAc/hexanes) to yield (S)-benzyl 2-((2R,6R)-2,6-dimethyltetrahydro-2H-pyran-4-yl)-2-(methoxycarbonylamino)acetate (Cap-2, step e) (56 mg) as a colorless glass. LC-MS retention time 3.338 min; m/z 335.99 [M+H]$^+$. LC data was recorded on a Shimadzu LC-10AS liquid chromatograph equipped with a Phenomenex-Luna 3u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode. $^1$H NMR (400 MHz, D$_4$-MeOH) δ ppm 7.29-7.42 (m, 5H), 5.28 (d, J=12.0 Hz, 1H), 5.09 (d, J=12.0 Hz, 1H), 4.10-4.20 (m, 2H), 3.68-3.78 (m, 1H), 3.65 (s, 3H), 2.22-2.36 (m, 1H), 1.42-1.54 (m, 2H), 1.29-1.38 (m, 1H), 1.17 (d, J=6.8 Hz, 3H), 1.04 (d, J=6.0 Hz, 3H), 0.89-1.00 (m, 1H).

Cap-2

(S)-Benzyl 2-((2R,6R)-2,6-dimethyltetrahydro-2H-pyran-4-yl)-2-(methoxycarbonylamino)acetate (Cap-2, step e) (56 mg, 0.167 mmol) was dissolved in MeOH (4 mL) and then treated with 10% Pd/C (12 mg, 0.012 mmol). The reaction mixture was vacuum flushed with nitrogen (4×) and then with hydrogen (4×) and stirred under a balloon of hydrogen overnight. The reaction was filtered through Celite® and concentrated to yield (S)-2-((2R,6R)-2,6-dimethyltetrahydro-2H-pyran-4-yl)-2-(methoxycarbonylamino)acetic acid (Cap-2) (41 mg) as a colorless oil. ¹H NMR (400 MHz, D₄-MeOH) δ ppm 4.22 (quin, J=6.4 Hz, 1H), 4.04-4.11 (m, 1H), 3.78-3.87 (m, 1H), 3.66 (s, 3H), 2.26-2.39 (m, 1H), 1.63 (d, J=13.1 Hz, 1H), 1.51-1.60 (m, 1H), 1.42-1.49 (m, 1H), 1.27 (d, J=7.0 Hz, 3H), 1.11 (d, J=6.3 Hz, 3H), 0.97-1.08 (m, 1H).

Note: The absolute stereochemistry of Cap-2 was determined by single crystal X-ray analysis of an amide analog prepared from an epimer of Cap-2 ((R)-2-((2R,6R)-2,6-dimethyltetrahydro-2H-pyran-4-yl)-2-((methoxycarbonyl)amino)acetic acid) and (S)-1-(naphthalen-2-yl)ethanamine An alternative synthesis of Cap-2 is illustrated in Scheme-1. The first four steps resulting in (R)-2-methyl-2H-pyran-4 (3H)-one were performed using adaptations of a reported procedure (Anderson, K. R; et al. *Org. Proc. Res. Dev.* 2010, 14, 58). The conversion of (R)-2-methyl-2H-pyran-4(3H)-one to (2R,6R)-2,6-dimethyldihydro-2H-pyran-4(3H)-one was accomplished with adaptations of a reported procedure (Reddy, D. S.; et al. *J. Org. Chem.* 2004, 69, 1716). Additional details are provided below.

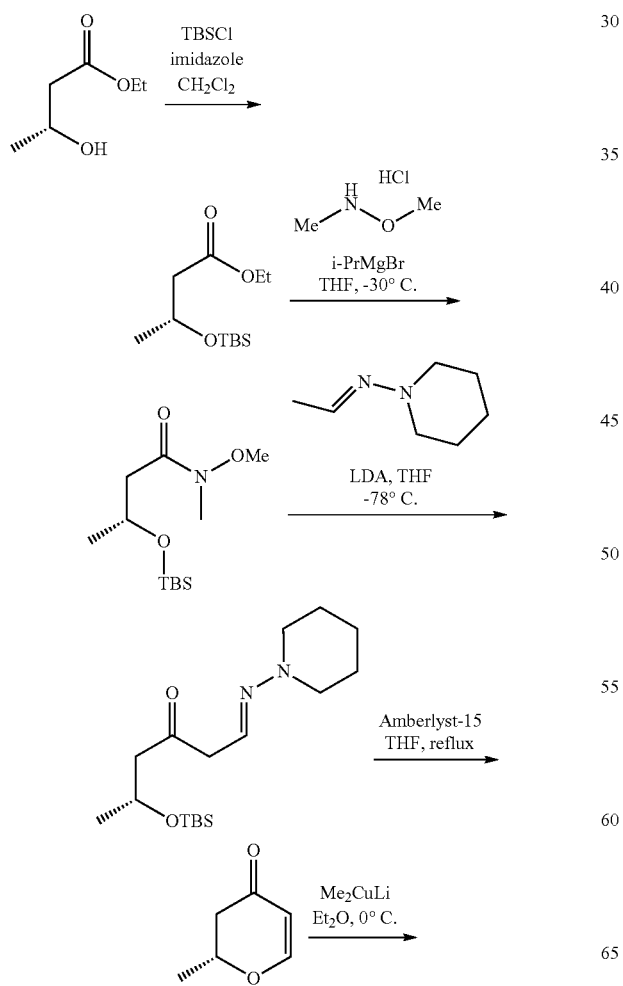

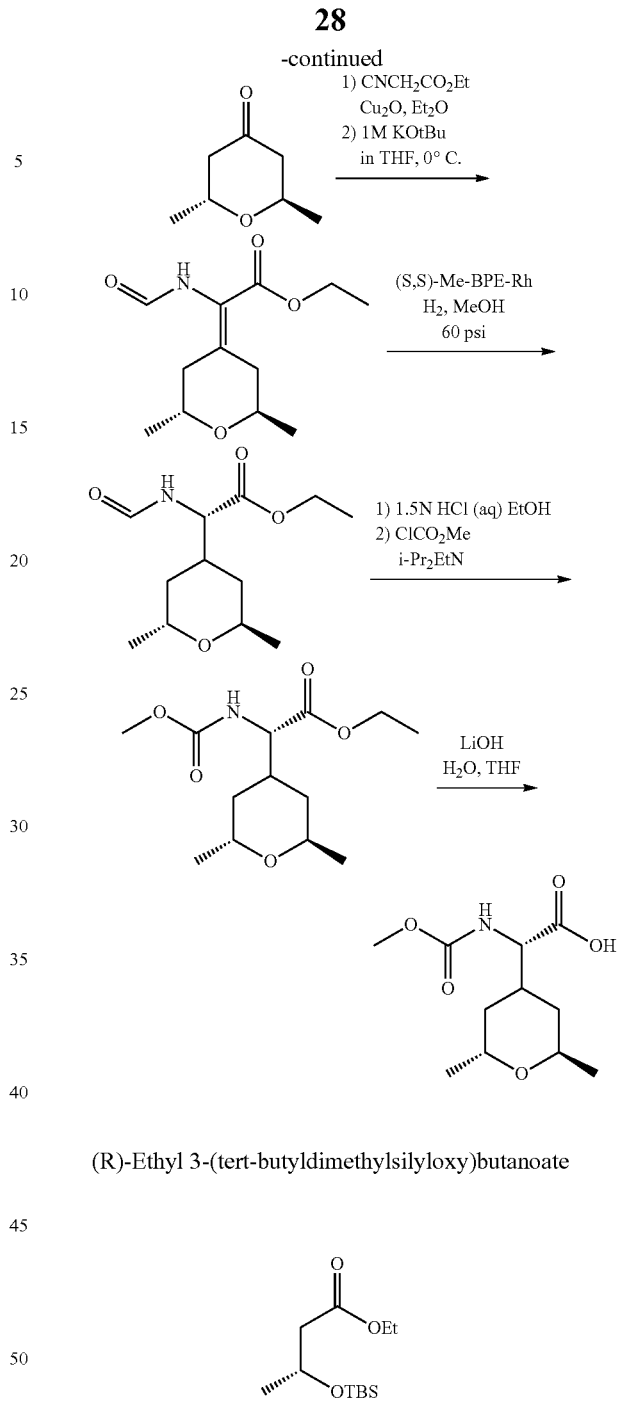

(R)-Ethyl 3-(tert-butyldimethylsilyloxy)butanoate tert-Butylchlorodimethylsilane (547 g, 3.63 mol) was added to a stirred solution of (R)-ethyl 3-hydroxybutanoate (400 g, 3.03 mol) in DCM (800 mL) under nitrogen at 0° C. Imidazole (412 g, 6.05 mol) was added portion wise over 20 min to the reaction mixture during which time the mixture became a thick white slurry. Additional DCM (175 mL) was added and the mixture was allowed to warm to room temperature and stirred for 16 h. The white solid was removed by filtration, rinsed with DCM (500 mL), partitioned between water (1 L) and DCM (500 mL), and the aqueous layer was further extracted with additional DCM (500 mL). The filtrate was combined with the organic layers and washed with water (500 mL) and brine, dried over MgSO₄ and filtered. The product was concentrated and dried under high vacuum to yield (R)-ethyl 3-(tert-butyldimethylsilyloxy)butanoate (777.5 g), containing unidentified impurities. The analytical data of the crude product complied with data reported in the literature. The material was used without additional purification.

(R)-3-(tert-Butyldimethylsilyloxy)-N-methoxy-N-methylbutanamide

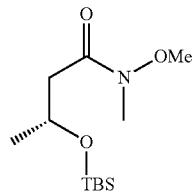

A solution of 2M isopropylmagnesium chloride in THF (800 mL, 1.60 mol) was added dropwise via cannula over 60 min to a stirred solution of (R)-ethyl 3-(tert-butyldimethylsilyloxy)butanoate (131 g, 532 mmol) and N,O-dimethylhydroxylamine/HCl (80 g, 824 mmol) in dry THF (850 mL) while maintaining the internal temperature between −30° C. and −20° C. The suspension was allowed to stir for 3 h between −20 and −10° C., and quenched while cold with saturated aqueous ammonium chloride solution (400 mL). The reaction mixture was partitioned between water (200 mL) and diethyl ether (500 mL) and the aqueous phase was further extracted with diethyl ether (1 L). The combined organic phases were washed with brine, dried over MgSO$_4$, filtered, concentrated and dried under high vacuum to yield (R)-3-(tert-butyldimethylsilyloxy)-N-methoxy-N-methylbutanamide. The reaction was repeated 6 times to yield a total of 717 g material. The analytical data complied with data reported in the literature. The material was used without additional purification.

N-Ethylidenepiperidin-1-amine

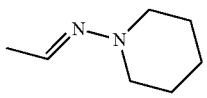

For relevant references, see: (a) Marques-Lopez, E.; et al. *Eur. J. Org. Chem.* 2008, 20, 3457. (b) Corey, E.; et al. *Chem. Ber.* 1978, 111, 1337. (c) Chudek, J. A. et al. *J. Chem. Soc. Perkin Trans* 2 1985, 8, 1285.

Piperidin-1-amine (754 mL, 6.99 mol) was added dropwise over 60 min to acetaldehyde maintained at a 0° C. (304 mL, 5.38 mol) while stirring under nitrogen. [Caution: The addition is exothermic. On this scale, the dropping funnel containing piperidin-1-amine became hot due to acetaldehyde that had vaporized and condensed in the dropping funnel]. After 1 h at 0° C. and 1 h at rt, the reaction flask was equipped with a 16-in reflux condenser and was warmed to 40° C. and stirred for 20 h. The reaction mixture was cooled to RT and partitioned between diethyl ether (700 mL) and brine (300 mL). The organic layer was washed with water and the aqueous layer was extracted with diethyl ether (2×500 mL). The combined organic layers were washed with brine, dried over MgSO$_4$, filtered, concentrated and dried under high vacuum for 8 h to afford (E)-N-ethylidenepiperidin-1-amine (772 g) (contained impurities) as a yellow oil. The analytical data complied with data reported in the literature. The material was used without additional purification.

(E)-5-((R)-tert-Butyldimethylsilyloxy)-1-(piperidin-1-ylimino)hexan-3-one

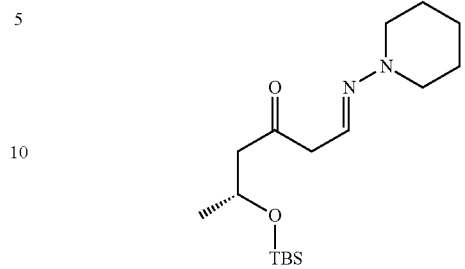

n-BuLi in hexanes (2.5 M, 644 mL, 1.61 mol) was added over 40 min to a stirred solution of diisopropylamine (245 mL, 1.72 mol) in dry THF (2.3 L) at 0° C. under nitrogen. The mixture was stirred at 0° C. for 30 min and then a solution of (E)-N-ethylidenepiperidin-1-amine (203 g, 1.61 mol) in dry THF (100 mL) was added dropwise. The reaction mixture was stirred at 0° C. for 2 h and the suspension cooled to −78° C. and treated dropwise with a solution of (R)-3-(tert-butyldimethylsilyloxy)-N-methoxy-N-methylbutanamide (280.4 g, 1.073 mol) in dry THF (100 mL). The reaction mixture was stirred for 3 h at −78° C., allowed to slowly warm to room temperature and then stirred for 16 h. The reaction mixture was partitioned between water (600 mL) and diethyl ether (1.5 L), and the aqueous layer was further extracted with diethyl ether. The combined organic layers were washed with brine, dried over MgSO$_4$, filtered and concentrated to yield an amber-colored oil. The crude oil was purified through a short column (3 L silica gel in a 4 L sintered glass funnel was pre-equilibrated with 5% EtOAc/hexanes, then the crude oil was dissolved in 50 mL of DCM/hexanes (1:5) and loaded onto the top of the silica gel, and, finally, the column was eluted with 5-40% EtOAc/hexanes) to yield (E)-5-((R)-tert-butyldimethylsilyloxy)-1-(piperidin-1-ylimino)hexan-3-one. Impure fractions were combined, concentrated and repurified with a Biotage® Horizon (300 g SiO$_2$, 15-45% EtOAc/hexanes) to yield additional product (230 g total). The analytical data complied with data reported in the literature. The material was used without additional purification.

(R)-2-Methyl-2H-pyran-4(3H)-one

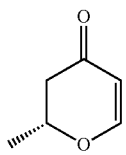

Amberlyst-15 (122 g, 372 mmol) (dry form, pale brown beads, Alfa Aesar, Stock #89079 or L14146) was added in one portion to a stirred solution of (E)-5-((R)-tert-butyldimethylsilyloxy)-1-(piperidin-1-ylimino)hexan-3-one (121 g, 372 mmol) in dry THF (1.2 L). The mixture was refluxed for 2.5 h, cooled, filtered, and concentrated to an amber-colored liquid. The crude liquid was purified through a short column (the crude product was dissolved in 30 mL of 5% EtOAc/hexanes and loaded onto the top of 1.5 L of silica gel in a 4 L sintered glass funnel that was pre-equilibrated with 5% EtOAc/hex, and the column was eluted with 5-50% EtOAc/hexanes) to yield enone (R)-2-methyl-2H-pyran-4(3H)-one. Note: The solvent was removed by careful rotary evaporation (bath temperature was less than or equal to ambient temperature) but some desired product was detected in the recovery trap. This material was concentrated to remove solvent using a 20-inch Vigreux column with a distillation head and combined with the original material. The total desired product was further purified by distillation to afford a colorless oil (17.8 g) with boiling point of 68-70° C. at 10 mm Hg. Optical Rotation: +212.8 at c=0.46 g/100 mL CHCl₃.

(2R,6R)-2,6-Dimethyldihydro-2H-pyran-4(3H)-one

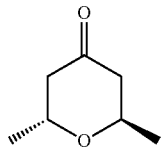

Methyllithium in diethyl ether (1.6M, 218 mL, 349 mmol) was added in ~10 mL portions over 20 min to a stirred slurry of copper(I) iodide (44.3 g, 233 mmol) in diethyl ether (350 mL) cooled to 0° C. under nitrogen. The reaction mixture was stirred at 0° C. for 30 min and then (R)-2-methyl-2H-pyran-4(3H)-one (13.5 g, 116 mmol) in diethyl ether (150 mL) was added dropwise over 30 min. The cold bath was removed and the reaction mixture was allowed to warm to rt and stirred for 3 h. The reaction mixture was slowly added (over ~5 min) to a stirred solution of sat. NH₄Cl (aq) (~750 mL) and ice. Additional diethyl ether (~500 mL) and water (~150 mL) were added and the solution, which contained a grey precipitate, was stirred overnight. The layers were separated and the aqueous layer was extracted with diethyl ether (500 mL) and DCM (500 mL). The combined organic phase was dried (MgSO₄), filtered and concentrated (the rotary evaporator bath temperature was held at or below ambient temperature) to an orange oil. The crude oil was purified with a Biotage® Horizon (240 g SiO₂, 1-4% diethyl ether in DCM, column was pre-equilibrated with DCM) to yield (2R,6R)-2,6-dimethyldihydro-2H-pyran-4(3H)-one (13.4 g, 86% pure by ¹H-NMR) as a light yellow oil. [Note: The material was carefully concentrated and contained 10% w/w DCM by ¹H-NMR. ¹H-NMR analysis also indicated that the material was contaminated with ~2.5% TBDMSOH carried over from a previous reaction and 1.6% of (2R,6S)-2,6-dimethyldihydro-2H-pyran-4(3H)-one]. The analytical data of the product complied with the data reported in the literature, and the material was used without additional purification. ¹H-NMR (400 MHz, CDCl₃) δ 4.41-4.25 (m, 2H), 2.55 (ddd, J=14.1, 4.8, 1.4 Hz, 2H), 2.24 (ddd, J=14.1, 6.5, 1.5 Hz, 2H), 1.28 (d, J=6.5 Hz, 6H).

Ethyl 2-((2R,6R)-2,6-dimethyl-2H-pyran-4(3H,5H,6H)-ylidene)-2-formamidoacetate

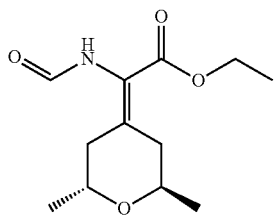 [SMILES: CCOC(=O)C(NC=O)=C1C[C@@H](C)O[C@H](C)C1]

Cuprous oxide (2.21 g, 15.4 mmol) was added to a stirred solution of ethyl 2-isocyanoacetate (12.7 mL, 116 mmol) in diethyl ether (300 mL) and the slurry was vigorously stirred for 10 min. (2R,6R)-2,6-Dimethyldihydro-2H-pyran-4(3H)-one (15.2 g, 103 mmol, 87% purity with 13% w/w DCM) in diethyl ether (100 mL) was added over 15 min and the reaction mixture was stirred at RT for 2 h. The reaction mixture was cooled to 0° C. and treated with 1M KO-tBu (116 mL, 116 mmol) in THF added in 10 mL portions over ~15 min and then stirred at 0° C. for 1 h. A solution of acetic acid (6.66 mL, 116 mmol) in DCM (60 mL) was added and the reaction mixture was allowed to warm to RT and stirred for 2 h. The crude reaction mixture was partitioned between water (~300 mL) and diethyl ether (~300 mL) and the aqueous layer was further extracted with DCM (300 mL). The combined organic phase was dried (MgSO₄), filtered and concentrated to a dark red oil, which solidified under vacuum. The crude material was purified with a Biotage® Horizon chromatography (300 g SiO₂; loaded onto column using a minimal amount of DCM; eluted with 40-60% EtOAc/hexanes, holding at 40% for four column volumes). The early fractions of desired product also contained the cis-stereoisomer version of the target product as an impurity. These impure fractions were combined, concentrated to give 8.9 g of a light yellow oil that was repurified with a Biotage® Horizon chromatography (240 g silica gel; eluted with 40-65% EtOAc/hexanes, holding at 40% for five column volumes). All fractions with clean desired product from both purifications, as determined by TLC, were combined and concentrated to yield ethyl 2-((2R,6R)-2,6-dimethyl-2H-pyran-4(3H,5H,6H)-ylidene)-2-formamidoacetate (18.8 g) as a light yellow solid contaminated with <1% (HPLC) of the cis-dimethyl isomeric variant.

The ¹H- and ¹³C-NMR data for the pure material presents as a 2:1 mixture of amide rotamers: ¹H-NMR (400 MHz, CDCl₃) δ 8.24 (d, J=1.3 Hz, 0.66H), 7.98 (d, J=11.5 Hz, 0.33H), 6.71 (br. s., 0.66H), 6.56 (d, J=12.0 Hz, 0.33H), 4.32-4.00 (m, 4H), 3.05 (dd, J=14.3, 4.3 Hz, 0.33H), 2.92 (d, J=5.3 Hz, 1.33H), 2.82 (dd, J=14.3, 6.5 Hz, 0.33H), 2.62 (dd, J=13.9, 3.9 Hz, 0.33H), 2.45 (dd, J=14.1, 3.8 Hz, 0.66H), 2.24 (dd, J=13.8, 7.3 Hz, 0.33H), 2.14-2.04 (m, 0.66H), 1.37-1.29 (m, 3H), 1.28-1.18 (m, 6H). ¹³C-NMR (101 MHz, CDCl₃) δ 164.5 (0.66C), 163.9 (0.33C), 163.8 (0.33C), 159.3 (0.66C), 147.5 (0.33C), 147.0 (0.66C), 120.3 (0.33C), 118.6 (0.66C), 68.1 (0.66C), 67.8 (0.33C), 67.4 (0.33C), 66.8 (0.66C), 61.1 (0.33C), 60.9 (0.66C), 38.2 (0.66C), 37.4 (0.33C), 36.2 (0.33C), 36.0 (0.66C), 20.5 (0.66C), 20.1 (0.33C), 19.5 (0.33C), 19.2 (0.66C), 13.8 (s, 1C). LC-MS retention time 1.85 min; m/z 242.45 (M+H)⁺. LC data was recorded on a Shimadzu LC-10AS liquid chromatograph equipped with a Phenomenex-Luna 3µ C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min. Solvent A was 10% acetonitrile/90% H₂O/0.1% trifluoroacetic acid, and solvent B was 10% H₂O/90% acetonitrile/0.1% trifluoroacetic acid. MS data was determined using a Micromass Platform for LC in electrospray mode.

(S)-Ethyl 2-((2R,6R)-2,6-dimethyltetrahydro-2H-pyran-4-yl)-2-formamidoacetate

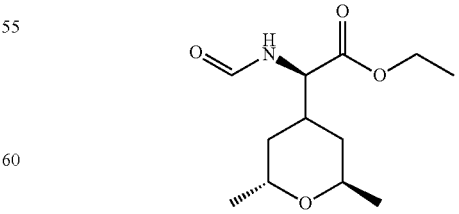

Nitrogen was bubbled through a solution of ethyl 2-((2R, 6R)-2,6-dimethyl-2H-pyran-4(3H,5H,6H)-ylidene)-2-formamidoacetate (17.0 g, 70.5 mmol) in MeOH (480 mL) for 10 min in a 2.5 L Parr hydrogenation vessel. Then (−)-1,2- bis((2S,5S)-2,5-dimethylphospholano)ethane(cyclooctadiene)-rhodium (I) tetrafluoroborate (0.706 g, 1.27 mmol) was added and the reaction vessel was sealed, vacuum flushed with nitrogen (4×) and then vacuum flushed with hydrogen (4×). The reaction solution was shaken under 60 psi of hydrogen for 3 d, removed from the shaker and concentrated to a dark red oil. The crude oil was purified with a Biotage® Horizon chromatography (300 g SiO$_2$, 50-75% EtOAc/hexanes) to yield (S)-ethyl 2-((2R,6R)-2,6-dimethyltetrahydro-2H-pyran-4-yl)-2-formamidoacetate (17.4 g, contains 5.9% w/w solvents (EtOAc and DCM) by $^1$H-NMR) as a light yellow viscous oil. The $^1$H-NMR data indicates a 10:1 mixture of two amide rotamers. $^1$H-NMR (400 MHz, CDCl$_3$) δ 8.26 (s, 0.9H), 8.01 (d, J=11.8 Hz, 0.1H), 6.15 (d, J=8.5 Hz, 0.9H), 5.96-5.84 (m, 0.1H), 4.68 (dd, J=9.0, 5.0 Hz, 0.9H), 4.33-4.17 (m, 3H), 3.87 (dd, J=10.2, 6.4 Hz, 0.1H), 3.75 (dqd, J=11.5, 6.0, 2.0 Hz, 1H), 2.41-2.29 (m, 0.9H), 2.29-2.19 (m, 0.1H), 1.72-1.28 (m, 3H), 1.28-1.23 (m, 6H), 1.17-1.10 (m, 3H), 1.09-0.96 (m, 1H). $^{13}$C-NMR (101 MHz, CDCl$_3$) δ 170.6, 160.3, 68.1, 64.0, 61.4, 54.2, 36.0, 33.1, 30.6, 21.9, 16.7, 13.9. LC-MS retention time 1.64 min; m/z 244.25 (M+H)$^+$. LC data were recorded on a Shimadzu LC-10AS liquid chromatograph equipped with a Phenomenex-Luna 3μ C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min. Solvent A was 10% acetonitrile/90% H$_2$O/0.1% trifluoroacetic acid, and solvent B was 10% H$_2$O/90% acetonitrile/0.1% trifluoroacetic acid. MS data were determined using a Micromass Platform for LC in electrospray mode.

(S)-Ethyl 2-((2R,6R)-2,6-dimethyltetrahydro-2H-pyran-4-yl)-2-(methoxycarbonylamino)acetate

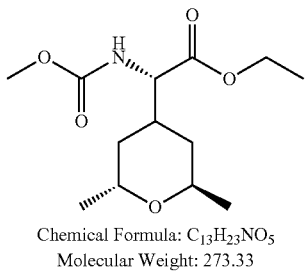 [SMILES: CCOC(=O)[C@@H](NC(=O)OC)C1C[C@@H](C)O[C@H](C)C1]

Chemical Formula: C$_{13}$H$_{23}$NO$_5$
Molecular Weight: 273.33

In a 1 L flask equipped with a condenser which was stoppered with a septum and vented with a needle, a solution of (S)-ethyl 2-((2R,6R)-2,6-dimethyltetrahydro-2H-pyran-4-yl)-2-formamidoacetate (17.6 g, 72.3 mmol) in ethanol (409 mL) and 1.5 N HCl (aq) (409 mL) was heated in a pre-equilibrated oil bath at 52° C. for 7.5 h. The volatile component was removed under vacuum and the residue was azeotroped with EtOH (2×50 mL) and dried under vacuum overnight to afford a white foam. The white foam was dissolved into DCM (409 mL) and N,N-diisopropylethylamine (38.0 mL, 218 mmol) was added dropwise over 10 min followed by methyl chlorocarbonate (8.40 mL, 109 mmol), also added dropwise over 10 min. The reaction mixture was stirred at ambient temperature for 4.5 h and then quenched carefully with 1 N HCl (100 mL). The layers were separated and the organic layer was washed with 1 N HCl (50 mL) and then with an aqueous basic solution (50 mL water+2 mL sat. NaHCO$_3$). The organic layer was dried (MgSO$_4$), filtered, and concentrated. The residue was purified with a Biotage® (300 g SiO$_2$; sample was loaded onto column with a minimal amount of chloroform, and eluted with 30% EtOAc/hexanes) to yield (S)-ethyl 2-((2R,6R)-2,6-dimethyltetrahydro-2H-pyran-4-yl)-2-(methoxycarbonyl-amino)acetate (13.8 g) as a viscous yellow oil. $^1$H-NMR (400 MHz, CDCl$_3$) δ 5.23 (d, J=8.8 Hz, 1H), 4.34-4.15 (m, 4H), 3.81-3.72 (m, 1H), 3.70 (s, 3H), 2.35-2.23 (m, 1H), 1.63-1.51 (m, 2H), 1.34-1.27 ('m' & 't' overlapped, J=7.0 Hz, 1H & 3H), 1.25 (d, J=6.8 Hz, 3H), 1.14 (d, J=6.0 Hz, 3H), 1.11-0.99 (m, 1H). LC-MS retention time 2.89 min; m/z 296.23 (M+Na)$^+$. LC data were recorded on a Shimadzu LC-10AS liquid chromatograph equipped with a Phenomenex-Luna 3μ C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min. Solvent A was 10% MeOH/90% H$_2$O/0.1% trifluoroacetic acid, and solvent B was 10% H$_2$O/90% MeOH/0.1% trifluoroacetic acid. MS data were determined using a Micromass Platform for LC in electrospray mode.

Additional note: the above product was further purified by SFC chromatography (180 mg/injection, with a throughput of 7.2 g/hr) prior to the hydrolysis step to remove an unidentified impurity. Conditions:

Column: ChiralPak AD-H 25×3 cm, 5μ
Column Temperature: 25° C.
Flow rate: 150 mL/min
Mobile Phase: CO$_2$/MeOH=93/7
Injection Volume: 1.0 mL (180 mg/mL)
Injection Model: Stacked (injection/run time (min)=1.47/3.0)
Detector Wavelength: 220 nm
Sample Solvent: CH$_3$OH/CH$_3$CN=1:1(v/v)

(S)-2-((2R,6R)-2,6-Dimethyltetrahydro-2H-pyran-4-yl)-2-(methoxycarbonylamino) acetic acid (Cap-2)

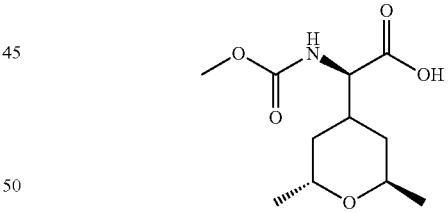

Lithium hydroxide hydrate (8.51 g, 203 mmol) in H$_2$O (270 mL) was added dropwise to a stirred solution of (S)-ethyl 2-((2R,6R)-2,6-dimethyltetrahydro-2H-pyran-4-yl)-2-(methoxycarbonyl-amino)acetate (27.7 g, 101 mmol) in THF (405 mL) over 65 min, while maintaining an internal temperature <5° C. The reaction mixture was stirred in an ice bath for 40 min and then in a water bath at RT for 5 h. The reaction mixture was partially concentrated to remove the THF and then partitioned between water (250 mL) and DCM (250 mL). The aqueous layer was adjusted to pH=2 with 1 N HCl (205 mL), and then extracted with isopropyl acetate (7×250 mL). The combined extracts were washed with brine (1×600 mL), dried (MgSO$_4$), filtered and concentrated. The resulting viscous oil was treated with toluene (100 mL) and ether (75 mL), evaporated and dried in vacuo to afford Cap-2 (25.8 g, with 0.33 eq. of toluene) as a white foam. Chiral SFC purity >99.9% (Chiralpak AD-H (25×0.46 cm, 5 μm) 5% EtOH in CO$_2$, 3 mL/min, 35° C., 220 nm, 100 bar). HPLC purity 95.6% (Column: Sunfire C8 75×4.6 mm ID; 2.5 μm; 40° C.; Mobile Phase: A=Water w/0.1% Formic Acid; B=CH$_3$CN w/0.1% Formic Acid). LC/MS (ES+) 228.1 (M+H—H$_2$O)$^+$. By $^1$H-NMR the material contained about 0.33 eq. of toluene. $^1$H-NMR (400 MHz, CDCl$_3$) δ 5.29 (d, J=8.6 Hz, 1H), 4.46- 4.25 (m, 2H), 3.82 (dd, J=9.7, 5.9 Hz, 1H), 3.74 (s, 3H), 2.46-2.30 (m, 1H), 1.76-1.55 (m, 2H), 1.51-1.35 (m, 1H), 1.29 (d, J=6.8 Hz, 3H), 1.18 (d, J=6.2 Hz, 3H), 1.18-1.06 (m, 1H). $^{13}$C-NMR (101 MHz, CDCl$_3$) δ 174.1, 156.7, 68.3, 64.4, 57.5, 52.2, 35.8, 32.6, 30.3, 21.6, 16.7.

EXAMPLE 1

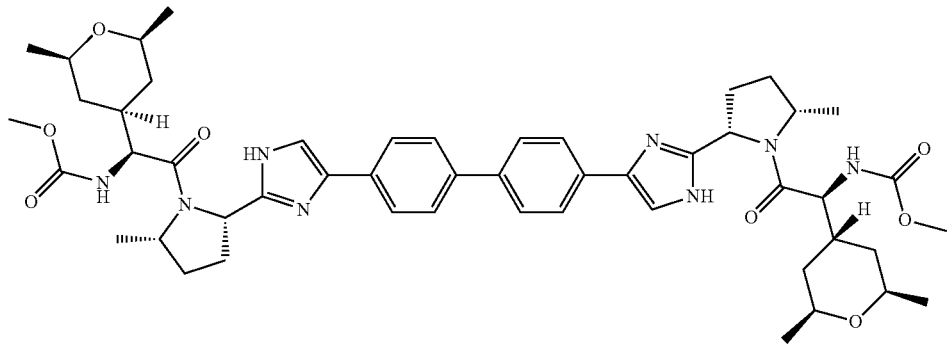

Dimethyl(4,4'-biphenyldiylbis(1H-imidazole-4,2-diyl((2S,5S)-5-methyl-2,1-pyrrolidinediyl)((1S)-1-((2R,6R)-2,6-dimethyltetrahydro-2H-pyran-4-yl)-2-oxo-2,1-ethanediyl))biscarbamate

EXAMPLE 1

Step a

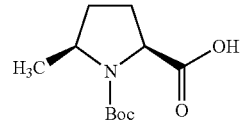 [SMILES: C[C@H]1CC[C@@H](C(=O)O)N1C(=O)OC(C)(C)C]

The above compound was synthesized according to a literature protocol (*J. Med. Chem.*, 2006, 49, 3520) with the following purification modifications: the crude material was recrystallized from EtOAc/hexanes at ambient temperature to afford Example 1, Step a, as a white crystal. $^1$H NMR (400 MHz, CDCl$_3$) δ ppm 4.32 (br m, 1H), 3.89 (br m, 1H), 2.40 (br m, 1H), 2.00 (m, 2H), 1.65 (m, 1H), 1.45 (s, 9H), 1.20 (d, J=5.6, 3H). LC/MS: Anal. Calcd. for [M+Na]$^+$ C$_{11}$H$_{20}$NO$_4$Na: 252.12. Found 252.21.

EXAMPLE 1

Step b

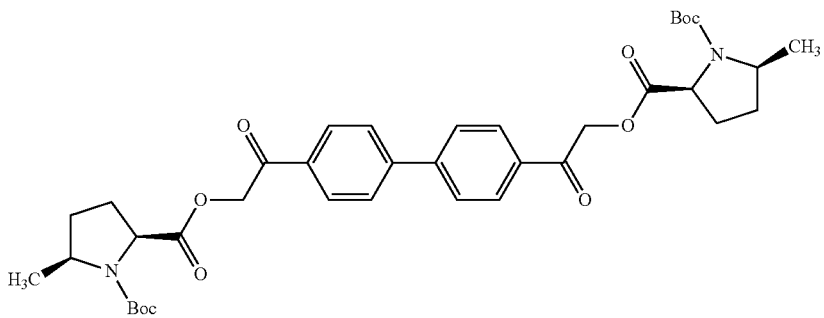

To a mixture of Example 1, step a (7.12 g, 31.1 mmol) and 1,1'-(biphenyl-4,4'-diyl)bis(2-bromoethanone) (6.0 g, 15 mmol) in acetonitrile (100 mL), i-Pr$_2$EtN (5.56 mL, 31.8 mmol) was added dropwise, and the reaction was stirred at room temperature for 3 hr. The volatile component was removed in vacuo and the residue was partitioned between CH$_2$Cl$_2$ (100 mL) and sat. aq. NaHCO$_3$ (100 mL). The organic layer was separated and washed with water and brine, dried (Na$_2$SO$_4$), filtered, and concentrated in vacuo to afford Example 1, step b as white foam (9.83 g), which was used in the next step without purification. $^1$H NMR (500 MHz, CDCl$_3$) δ ppm 8.01 (4H, t, J=7.32 Hz), 7.73 (4H, d, J=6.71 Hz), 5.18-5.66 (4H, m), 4.51 (1H, t, J=7.17 Hz), 4.42 (1H, t, J=7.32 Hz), 4.06 (1H, d, J=3.36 Hz), 3.95 (1H, d, J=5.19 Hz), 2.27-2.37 (4H, m), 2.01-2.17 (2H, m), 1.67-1.82 (2H, m), 1.39-1.52 (18H, m), 1.32 (6H, t, J=6.56 Hz). LC-MS: Anal. Calcd. for [M+H]$^+$ C$_{38}$H$_{49}$N$_2$O$_{10}$ 693.34. Found 693.34.

EXAMPLE 1

Step c

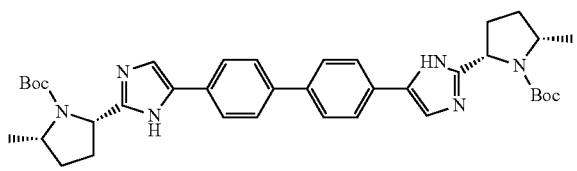

A mixture of Example 1, step b (9.83 g, 14.19 mmol) and ammonium acetate (10.94 g, 142 mmol) in xylene (160 mL) was heated in a pressure tube at 140° C. for 4 hours. The volatile component was removed in vacuo and the residue was partitioned between CH$_2$Cl$_2$ (140 mL) and water (100 mL). The organic layer was washed with saturated NaHCO$_3$ (100 mL), dried (Na$_2$SO$_4$) and concentrated in vacuo. The resultant crude material was purified via Biotage® (20% to 50% EtOAc/Hex; 300 g column) to afford Example 1, step c as light brown solid (4.3 g). $^1$H NMR (500 MHz, DMSO-d$_6$) δ ppm 11.73 (2H, br. s.), 7.83 (3H, d, J=7.63 Hz), 7.62-7.76 (5H, m), 7.27-7.55 (2H, m), 4.82 (2H, br. s.), 3.89 (2H, br. s.), 2.10 (6H, d, J=15.26 Hz), 1.58-1.89 (2H, m), 1.11-1.52 (24H, m). LC/MS: Anal. Calcd. for [M+H]$^+$ C$_{38}$H$_{49}$N$_6$O$_4$: 653.37. Found 653.60.

Alternative procedure: a mixture of Example 1, step b (157 g, 227 mmol), ammonium acetate (332 g, 4310 mmol), and imidazole (54.1 g, 795 mmol) in toluene (1.2 L) was heated at 80° C. for 1 h while sweeping the head space with nitrogen. The temperature was increased to 85° C. and the reaction mixture stirred for 18 h. The solvent was removed and the residue dissolved in DCM (2 L), washed with water (1 L) and sat. NaHCO$_3$ (3 L) and then dried (MgSO$_4$), filtered and concentrated. The residue was dissolved in MeOH (4 L), concentrated to ~900 mL and allowed to stand at rt. After 2 h, the precipitated solid was collected by filtration, washed with MeOH and dried to yield a white solid. This material was recrystallized from methanol (dissolve in 4 L, then reduced to ~0.9 L) and dried to afford Example 1, step c as a white solid (99.5 g). The crude compound from the mother liquor was purified by silica gel chromatography (300 g SiO$_2$, 20-50% EtOAc/hexanes) to yield additional product as a white solid (13.0 g).

EXAMPLE 1

Step d

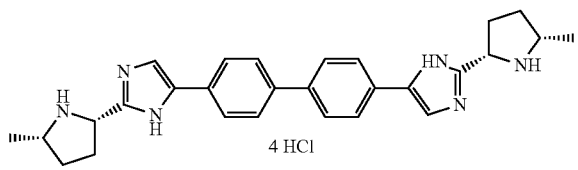

4 N HCl in dioxane (8.23 mL, 32.9 mmol) was added dropwise to a CH$_2$Cl$_2$ (100 mL) solution of Example 1, Step c (4.3 g, 6.6 mmol), and the reaction mixture was stirred at room temperature for 3 hours. Removal of the volatile component in vacuo afforded the HCl salt of Example 1, step d as a yellow solid (3.6 g). $^1$H NMR (400 MHz, DMSO-d$_6$) δ ppm 10.55 (2H, br. s.), 9.73 (2H, br. s.), 8.12-8.26 (2H, m), 8.03 (4H, d, J=8.03 Hz), 7.92 (4H, d, J=6.02 Hz), 5.07 (2H, m, J=7.53 Hz), 3.82 (2H, br. s.), 2.53-2.65 (4H, m), 2.27 (2H, dd, J=12.42, 6.40 Hz), 1.85-1.99 (2H, m), 1.45 (6H, d, J=6.27 Hz). LC/MS: Anal. Calcd. for [M+H]$^+$ C$_{28}$H$_{33}$N$_6$: 453.28. Found 453.21.

The purity level of the above deprotected product could be enhanced by applying the following recrystallization procedure: 2-propanol (242 mL) was added through an addition funnel over 15 min to a solution of Example 1, step d (60.5 g, HPLC purity of 98.9%) in water (121 mL) stirring at 60° C., while maintaining an internal temperature between 50° C. and 60° C. The solution was stirred for an additional 5 min, the heating mantle was removed and the mixture stirred at ambient temperature overnight. The precipitated solid was collected by filtration, washed with 2-propanol and dried under house vacuum overnight to give a yellow solid (54.4 g) with HPLC purity of 99.7% (Column: BEH C18 150 mm (L)×2.1 mm (ID), 1.7 μm, Mobile Phase: A: 0.05% TFA in water; B: 0.05% TFA in ACN). KF 15.3 wt % (6.0 mol of H$_2$O).

EXAMPLE 1

HATU (1.60 g, 4.21 mmol) was added to a solution of an HCl salt of Example 1, step d (1.2 g, 2.0 mmol), Cap-1 (1.01 g, 4.11 mmol) and DIEA (2.1 mL, 12 mmol) in DMF (20 mL) and the resulting yellow solution was stirred at RT for 3 h. The mixture was diluted with EtOAc (75 mL) and washed with water (100 mL). The aqueous layer was back extracted with EtOAc (75 mL) and the combined organic layers were washed with 50% solution of sat. aqueous NaHCO$_3$ (100 mL), water (100 mL) and brine (100 mL). It was then dried (MgSO$_4$), filtered and concentrated. The remaining residue was diluted with CH$_3$OH and submitted to a reverse phase HPLC purification: Solvent A: 5% MeCN/95% water/10 nM NH$_4$OAc; Solvent B: 95% MeCN/5% water/10 nM NH$_4$OAc; Column. Sunfire Prep C18 50×300 mm 10u; Wavelength: 220 nM; Flow rate: 150 ml/min; Gradient: 0% B to 70% B over 25 min with a 5 min hold time. Concentration under vacuum, yielded dimethyl(4,4'-biphenyldiylbis(1H-imidazole-4,2-diyl((2S,5S)-5-methyl-2,1-pyrrolidinediyl) ((1S)-1-((2R,6R)-2,6-dimethyltetrahydro-2H-pyran-4-yl)-2-oxo-2,1-ethanediyl)))biscarbamate (Example 1) as an off-white foam (1.2 g). Crystallization from EtOAc/Petroleoum ether gave an amorphous off-white solid. $^1$H NMR (500 MHz, DMSO-d$_6$) (of the TFA salt) δ 7.92 (br. s., 8H), 7.59 (d, J=7.9 Hz, 2H), 5.03 (t, J=8.5 Hz, 2H), 4.69-4.60 (m, 2H), 4.00 (t, J=8.4 Hz, 2H), 3.55 (s, 6H), 3.36 (br. s., 1H), 3.33-3.26 (m, 2H), 3.21 (br. s., 2H), 2.37 (br. s., 1H), 2.26 (d, J=11.3 Hz, 1H), 1.95-1.81 (m, 3H), 1.65 (d, J=10.7 Hz, 2H), 1.48 (d, J=6.4 Hz, 6H), 1.28-1.23 (m, 4H), 1.10-0.99 (m, 16H), 0.90-0.75 (m, 4H)

LC/MS: Anal. Calcd. for [M+H]$^+$ $C_{50}H_{67}N_8O_8$: 907.51. Found 907.8. Rt=3.99 min & >95% homogeneity index under the following LC condition—Column: Phenomenex-Luna 2.0×50 mm 3 um; Start % B=0; Final % B=100; Gradient Time=10 min; Flow Rate=4 mL/Min; Wavelength=220; Solvent A=H$_2$O:ACN 95%:5% 10 mm Ammonium Acetate; Solvent B=H$_2$O:ACN 5%:95% 10 mm Ammonium Acetate.

EXAMPLE 2

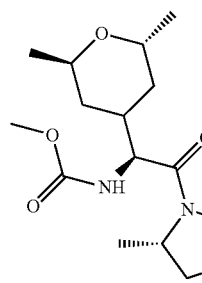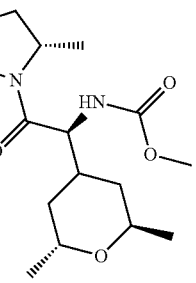

Dimethyl(4,4'-biphenyldiylbis(1H-imidazole-4,2-diyl((2S,5S)-5-methyl-2,1-pyrrolidinediyl)((1S)-1-((2R,6R)-2,6-dimethyltetrahydro-2H-pyran-4-yl)-2-oxo-2,1-ethanediyl)))biscarbamate HATU (63.6 mg, 0.167 mmol) was added to a stirred solution of (S)-2-((2R,6R)-2,6-dimethyltetrahydro-2H-pyran-4-yl)-2-(methoxycarbonylamino)acetic acid (Cap-2) (41 mg, 0.17 mmol) and the HCl salt of Example 1, step d (45.5 mg, 0.076 mmol) in DMF (0.9 mL) and DIPEA (0.11 mL, 0.61 mmol). The reaction mixture was stirred at RT for 4 h and then concentrated under a stream of nitrogen ON. The residue was dissolved in MeOH, filtered and purified by prep HPLC (Phenomenex Luna C18(2) 100×30 mm, 10 micron; MeOH/water w/ TFA buffer) to afford the TFA salt of dimethyl(4,4'-biphenyldiylbis(1H-imidazole-4,2-diyl((2S,5S)-5-methyl-2,1-pyrrolidinediyl)((1S)-1-((2R,6R)-2,6-dimethyltetrahydro-2H-pyran-4-yl)-2-oxo-2,1-ethanediyl)))biscarbamate (Example 2) (62.5 mg) as a light yellow solid. $^1$H NMR indicates the presence of a mixture of rotamers; for the major rotamer: $^1$H NMR (400 MHz, MeOH-d$_4$) δ 8.02-7.93 (m, 3H), 7.88 (br s, 7H), 5.18 (dd, J=10.7, 7.2 Hz, 2H), 4.77 (quin, J=6.6 Hz, 2H), 4.27-4.17 (m, 2H), 4.15 (d, J=9.3 Hz, 2H), 3.72-3.66 (m, 2H), 3.67 (s, 6H), 2.72-2.50 (m, 2H), 2.48-2.16 (m, 6H), 1.99 (dd, J=12.2, 5.6 Hz, 2H), 1.76-1.59 (m, 2H), 1.57 (d, J=6.5 Hz, 6H), 1.52-1.40 (m, 2H), 1.30 (dd, J=9.7, 6.7 Hz, 2H), 1.22 (d, J=6.8 Hz, 6H), 1.06 (d, J=6.0 Hz, 6H), 0.97 (app q, J=12.0 Hz, 2H). LC-MS retention time 3.84 min; m/z 905.38 [M−H]$^−$. LC data was recorded on a Shimadzu LC-10AS liquid chromatograph equipped with a Phenomenex-Luna 3u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 5% MeOH/95% H$_2$O/10 mM ammonium acetate and solvent B was 5% H$_2$O/95% MeOH/10 mM ammonium acetate. MS data was determined using a Micromass Platform for LC in electrospray mode.

Alternatively, Example 2 could be prepared as follows:

A mixture of (S)-2-((2R,6R)-2,6-dimethyltetrahydro-2H-pyran-4-yl)-2-(methoxycarbonylamino)acetic acid (Cap-2) (25.1 g, 91.0 mmol), 2-hydroxypyridine 1-oxide (10.12 g, 91 mmol) and EDC (19.0 g, 99.0 mmol) in DMSO (400 mL) was stirred at rt for 1 h. To this solution was added Example 1, step d (HCl salt; 29.2 g, 41.4 mmol) and the resulting yellow solution was cooled to 10° C. with a water/ice bath. Then i-Pr$_2$EtN (26.7 g, 207 mmol) was added to the reaction mixture and, after the addition was complete, the ice bath was removed. The reaction mixture was stirred at ambient temperature for 25.5 h before being quenched by pouring into an ice (1600 g) and water (400 mL) mixture. The mixture was stirred at ambient temperature for 3 h. The white solid was collected on a Buchner funnel through filtration and then dried under house vacuum with a stream of nitrogen passing through the top of the filter funnel overnight to give a wet solid (124 g). The wet solid was dissolved into DCM (500 mL), washed with water (3×250 mL), dried (MgSO$_4$), filtered and concentrated to give a light brown solid (39.5 g). This material was combined with similar material from another batch (total 44.4 g) and purified by chromatography using an ISCO device (2×330 g silica gel, 0-30% MeOH/DCM) to afford Example-2 (38.1 g) as a brown solid with an HPLC purity of 98.6%. The material was decolorized as follows: 43.1 g of material was dissolved in EtOH (500 mL) and then treated with activated charcoal (8.6 g). The mixture was heated at 50° C. for 1 h, the charcoal was removed by filtration (3 layers of filter paper) and the filter cake chased with additional EtOH (300 mL). The filtrate was evaporated to dryness and dried in vacuo with a warm water bath to afford an off-white solid (43.0 g). The product could be purified further by employing an SFC protocol:

SFC Purification Conditions:

Throughput: 1.2 g/hr

Amt per Injections 30 mg

Column: Princeton CN 25×3 cm, 5μ

Column Temperature: 45° C.

Flow rate: 200 mL/min

Mobile Phase: CO$_2$/[MeOH/DCM=1:1 (in v/v)]=80/20

Injection Volume: 2.5 mL (12 mg/mL)

Injection Model: Stacked (injection/run time (min)=1.5/3.2)

Detector Wavelength: 316 nm

Sample Solvent: CH$_3$OH/DCM=1:1 (v/v)

EXAMPLE 3

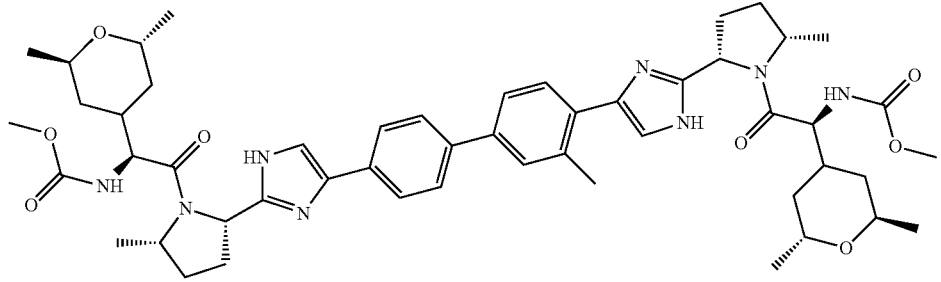

Dimethyl((3-methyl-4,4'-biphenyldiyl)bis(1H-imidazole-4,2-diyl((2S,5S)-5-methyl-2,1-pyrrolidinediyl)((1S)-1-((2R,6R)-2,6-dimethyltetrahydro-2H-pyran-4-yl)-2-oxo-2,1-ethanediyl))biscarbamate

EXAMPLE 3

Step a

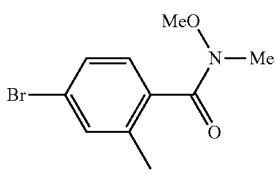

To a solution of 4-bromo-2-methylbenzoic acid (10 g, 46.5 mmol) in DMF (150 mL) was added N,O-dimethylhydroxylamine hydrochloride (5.44 g, 55.8 mmol) at RT followed by HOBT (8.55 g, 55.8 mmol). Then EDC (10.7 g, 55.8 mmol) was added followed by DIPEA (24.4 mL, 140 mmol) and the reaction mixture was stirred at RT for 12 h. The reaction mixture was then diluted with EtOAc (150 mL), washed with water (3×250 mL) and brine (150 mL), dried over $Na_2SO_4$, filtered and concentrated in vacuo to afford crude Example 3, step a (9.5 g), which was submitted to the next step as such. $^1$H NMR ($CDCl_3$, δ=7.26 ppm, 400 MHz): δ 7.37 (d, J=1.6 Hz, 1H), 7.34 (dd, J=8.0, 1.6 Hz, 1H), 7.14 (d, J=8.0 Hz, 1H), 3.47 (s, 3H), 3.30 (s, 3H), 2.31 (s, 3H). LC/MS: Anal. Calcd. For $[M+H]^+$ $C_{10}H_{13}{}^{81}BrNO_2$: 260.01. Found 260.0.

EXAMPLE 3

Step b

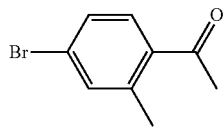

Example 3, step a (9.5 g, 36.8 mmol) was dissolved in diethyl ether (150 mL) and cooled to 0° C. Then methylmagnesium iodide (3.0 M in diethyl ether, 24.54 mL, 73.6 mmol) was added drop wise over 10 minutes. The reaction was stirred for 6 h at 40° C. and then brought to room temperature and stirred for 12 h. The reaction mixture was cooled to 0° C., quenched with ice and then with 1.5N HCl (50 mL). The organic layer was separated and the aqueous layer was extracted with methyl tert-butyl ether (2×100 mL), dried over $Na_2SO_4$ and concentrated under reduced pressure. The crude was purified by flash chromatography (Silica gel, 60-120, EtOAc: petroleum ether, 2:98) to afford Example 3, step b (6.25 g) as pale yellow liquid. $^1$H NMR ($CDCl_3$, δ=7.26 ppm, 400 MHz): δ 7.55 (d, J=8.0 Hz, 1H), 7.41 (s, 1H), 7.40 (d, J=8.0 Hz, 1H), 2.55 (s, 3H), 2.50 (s, 3H).

EXAMPLE 3

Step c

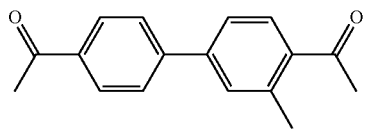 [SMILES: CC(=O)c1ccc(-c2ccc(C(C)=O)c(C)c2)cc1]

4-Acetylphenylboronic acid (5.39 g, 32.9 mmol) was added to a sealed tube containing Example 3, step b (7.0 g, 32.9 mmol) in MeOH (75.0 mL) and the reaction mixture was purged with nitrogen for 10 minutes. Then $K_2CO_3$ (9.08 g, 65.7 mmol) was added followed by $Pd(Ph_3P)_4$ (1.139 g, 0.986 mmol) and the reaction mixture was purged with nitrogen for further 10 minutes. The reaction mixture was heated to 75° C. for 12 h. Then the reaction mixture was concentrated under reduced pressure and the residue was diluted with EtOAc (100 mL) and washed with water (2×100 mL), brine (50 mL), dried over $Na_2SO_4$, filtered and concentrated under reduced pressure. The residue was purified by combiflash (Silicycle, $SiO_2$, 10-15% EtOAc/petroleum ether) to afford Example 3, step c (6.5 g) as a white solid. $^1$H NMR ($CDCl_3$, δ=7.26 ppm, 400 MHz): δ 8.06-8.04 (m, 2H), 7.81 (d, J=8.0 Hz, 1H), 7.72-7.70 (m, 2H), 7.54-7.49 (m, 2H), 2.65 (s, 3H), 2.63 (s, 6H).

EXAMPLE 3

Step d

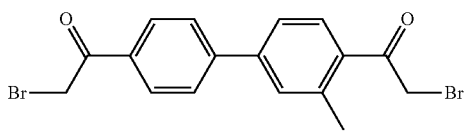

Bromine (1.12 mL, 21.8 mmol) (diluted in 10 mL of dioxane) was added slowly (over 10 minutes) to a solution of Example 3, step c (2.75 g, 10.90 mmol) in dioxane (50 mL) at 10° C., and the mixture was stirred at RT for 2 h. The reaction was quenched with 10% NaHCO$_3$ (25 mL) and extracted with DCM (50 mL). The organic phase was dried over Na$_2$SO$_4$ and concentrated under reduced pressure to afford crude Example 3, step d (5.0 g) which was used as such in the next step without purification. LC/MS: Anal. Calcd. For [M+H]$^+$ C$_{17}$H$_{15}$$^{79/81}$Br$_2$O$_2$: 410.94. Found 411.0.

EXAMPLE 3

Step e

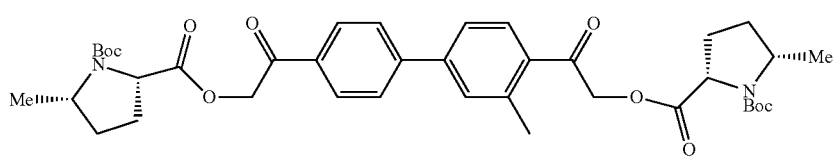 [SMILES: Cc1cc(-c2ccc(C(=O)COC(=O)[C@@H]3CC[C@H](C)N3C(=O)OC(C)(C)C)cc2)ccc1C(=O)COC(=O)[C@@H]1CC[C@H](C)N1C(=O)OC(C)(C)C]

To a solution of crude Example 3, step d (5.1 g, 12 mmol) in acetonitrile (75 mL) was added (2S,5S)-1-(tert-butoxycarbonyl)-5-methylpyrrolidine-2-carboxylic acid (Example 1, step a) (5.70 g, 24.9 mmol) followed by DIPEA (8.69 mL, 49.7 mmol) at 0° C. After 10 minutes, the temperature was raised to RT and stirred for 2 h. Then the reaction mixture was diluted with EtOAc (100 mL) and washed with 10% NaHCO$_3$ (50 mL), brine (50 mL), dried over Na$_2$SO$_4$, filtered and concentrated under reduced pressure. The residue was purified by combiflash (Silicycle, SiO$_2$, 25-30% EtOAc/petroleum ether) to afford Example 3, step e (5.8 g) as a pale yellow oil. $^1$H NMR (CDCl$_3$, δ=7.26 ppm, 400 MHz): δ 8.00 (app bd, 2H), 7.71 (app d, 3H), 7.53-7.51 (m, 2H), 5.61-5.34 (m, 2H), 5.29-5.04 (m, 2H), 4.51-4.36 (m, 2H), 4.09-3.91 (m, 2H), 2.59 (s, 3H), 2.35-2.21 (m, 4H), 2.15-2.04 (m, 2H), 1.80-1.63 (m, 2H), 1.47/1.44 (s, 18H), 1.35-1.27 (m, 6H). LC/MS: Anal. Calcd. for [M−H]$^−$ C$_{39}$H$_{49}$N$_2$O$_{10}$: 705.35. Found 705.30.

EXAMPLE 3

Step f

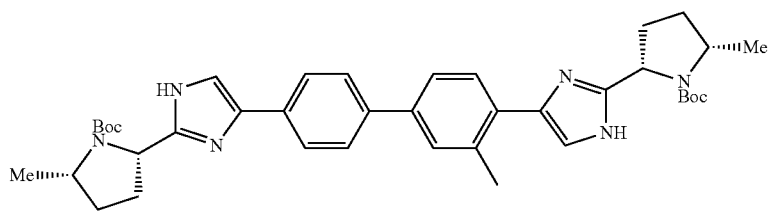 [SMILES: Cc1cc(-c2ccc(-c3c[nH]c([C@@H]4CC[C@H](C)N4C(=O)OC(C)(C)C)n3)cc2)ccc1-c1c[nH]c([C@@H]2CC[C@H](C)N2C(=O)OC(C)(C)C)n1]

To a solution of Example 3, step e (5.6 g, 7.92 mmol) in xylenes (75 mL) was added NH$_4$OAc (12.21 g, 158 mmol), and the reaction mixture was purged with nitrogen for 10 minutes. After heating for 18 h at 130° C., the reaction mixture was cooled to room temperature and the volatile components were removed under reduced pressure. Then the reaction mixture was diluted with EtOAc (100 mL) and washed with 10% NaHCO$_3$ (50 mL), brine (50 mL), dried over Na$_2$SO$_4$, filtered and concentrated under reduced pressure. The residue was purified by combiflash (Redi Sep, C-18 column, 30-40% acetonitrile: 10 mM ammonium bicarbonate) to afford Example 3, step f (2.3 g) as pale yellow solid. $^1$H NMR (DMSO-d$_6$, δ=2.50 ppm, 400 MHz): δ 12.27/12.0/11.77/11.71 (s, 2H), 7.92-7.63 (m, 5H), 7.58-7.47 (m, 3H), 7.24 (br s, 1H), 4.90-4.75 (m, 2H), 3.92-3.84 (m, 2H), 2.54 (s, 3H), 2.20-2.01 (m, 6H), 1.73-1.65 (m, 2H), 1.48-1.12 (m, 24H). LC/MS: Anal. Calcd. For [M−H]$^−$ C$_{39}$H$_{49}$N$_6$O$_4$: 665.39. Found 665.4.

EXAMPLE 3

Step g

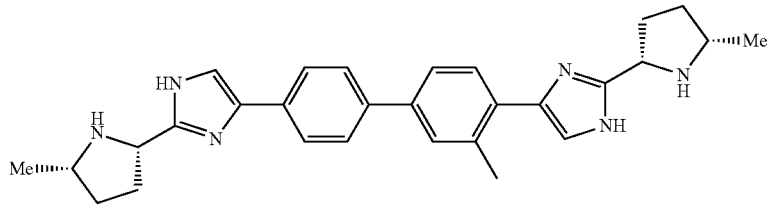 [SMILES: Cc1cc(-c2ccc(-c3c[nH]c([C@@H]4CC[C@H](C)N4)n3)cc2)ccc1-c1c[nH]c([C@@H]2CC[C@H](C)N2)n1]

To a solution of Example 3, step g (1.55 g, 2.32 mmol) in MeOH (10 mL) was added in HCl/MeOH (4N, 58.1 mL) and stirred at room temperature for 2 h. The volatile components were removed in vacuo, and the residue was co-evaporated with dry DCM (3×25 mL). The resulting solid was exposed to high vacuum to afford the HCl salt of Example 3, step g (1.3 g) as a pale yellow solid. $^1$H NMR (MeOD, $\delta$=3.34 ppm, 400 MHz): $\delta$ 8.06 (br s, 1H), 7.98 (d, J=8.4 Hz, 2H), 7.90 (d, J=8.4 Hz, 2H), 7.86 (br s, 1H), 7.78 (br s, 1H), 7.74 (d, J=8.4 Hz, 1H), 7.71 (d, J=8.4 Hz, 1H), 5.27-5.20 (m, 2H), 4.04-4.00 (m, 2H), 2.80-2.67 (m, 4H), 2.59 (s, 3H), 2.55-2.46 (m, 2H), 2.15-2.06 (m, 2H), 1.60 (d, J=6.4, 6H). LC/MS: Anal. Calcd. For $[[M+H]^+ C_{29}H_{35}N_6$: 467.28. Found 467.2.

EXAMPLE 3

HATU (60.5 mg, 0.159 mmol) was added to a stirred solution of (S)-2-((2R,6R)-2,6-dimethyltetrahydro-2H-pyran-4-yl)-2-(methoxycarbonylamino)acetic acid (Cap-2) (39 mg, 0.16 mmol) and the HCl salt of Example 3, step g (44.3 mg, 0.072 mmol) in DMF (0.9 mL) and DIPEA (0.10 mL, 0.58 mmol). The reaction mixture was stirred at RT for 2 h and concentrated under a stream of nitrogen overnight. The residue was diluted with MeOH, filtered and purified by prep HPLC (Phenomenex Luna C18(2) 100×30 mm, 10 micron; MeOH/water w/ TFA buffer) to afford the TFA salt of dimethyl((3-methyl-4,4'-biphenyldiyl)bis(1H-imidazole-4,2-diyl((2S,5S)-5-methyl-2,1-pyrrolidinediyl)((1S)-1-((2R,6R)-2,6-dimethyltetrahydro-2H-pyran-4-yl)-2-oxo-2,1-ethanediyl)))biscarbamate (Example 3) (60.2 mg) as an off-white solid. $^1$H NMR (400 MHz, MeOH-d$_4$) $\delta$ 8.01-7.84 (m, 5H), 7.78-7.54 (m, 4H), 5.75 (d, J=6.0 Hz, 0.4H), 5.19 (ddd, J=10.7, 6.9, 4.0 Hz, 1.6H), 4.84-4.72 (m, 2H), 4.36-4.12 (m, 4H), 3.85-3.58 (m, 8H), 2.69-1.95 (m, 13H), 1.75-1.40 (m, 10H), 1.37-1.02 (m, 14H), 0.96 (app q, J=12.2 Hz, 2H). LC-MS retention time 4.050 min; m/z 461.31 [½M+H]$^+$. LC data was recorded on a Shimadzu LC-10AS liquid chromatograph equipped with a Phenomenex-Luna 3u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 5% MeOH/95% water/10 mM ammonium acetate and solvent B was 5% water/95% MeOH/10 mM ammonium acetate. MS data was determined using a Micromass Platform for LC in electrospray mode.

EXAMPLE 4

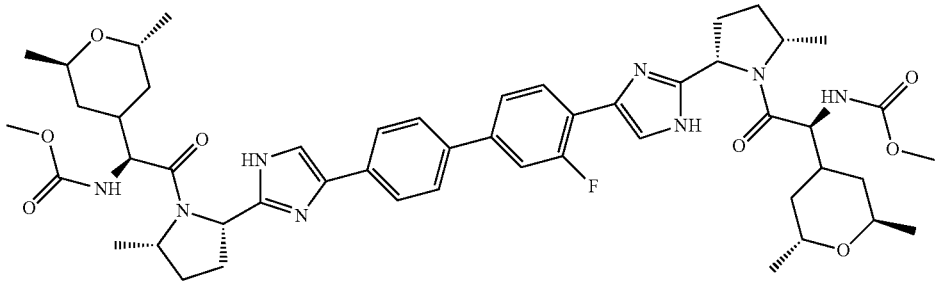

Dimethyl((3-fluoro-4,4'-biphenyldiyl)bis(1H-imidazole-4,2-diyl((2S,5S)-5-methyl-2,1-pyrrolidinediyl)((1S)-1-((2R,6R)-2,6-dimethyltetrahydro-2H-pyran-4-yl)-2-oxo-2,1-ethanediyl)))biscarbamate

EXAMPLE 4

Step a

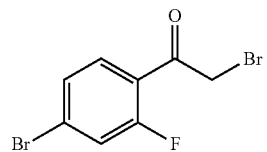 [SMILES: O=C(CBr)c1ccc(Br)cc1F]

To a solution of 1-(4-bromo-2-fluorophenyl)ethanone (5.0 g, 23 mmol) in dioxane (150 mL) and ether (150 mL) in a ice-water bath at 0° C. was added bromine (1.18 mL, 23.0 mmol) dropwise. The reaction was stirred for 1 hr, allowed to warm to RT and stirred for 16 hrs. The mixture was partitioned between EtOAc (50 mL) and sat. NaHCO$_3$ (50 mL), and the organic layer was washed with water and dried over Na$_2$SO$_4$. The volatile component was evaporated in vacuo and the solid was dried under vacuum overnight to afford Example 4, step a (6.94 g) as white solid. $^1$H NMR (DMSO-d$_6$, δ=2.5 ppm, 400 MHz): 7.87-7.79 (m, 2H), 7.62-7.60 (m, 1H), 4.84 (s, 2H).

EXAMPLE 4

Step b

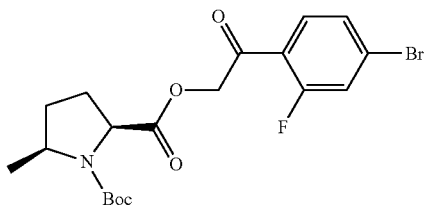 [SMILES: C[C@H]1CC[C@@H](C(=O)OCC(=O)c2ccc(Br)cc2F)N1C(=O)OC(C)(C)C]

To a solution of Example 4, step a (2.58 g, 8.72 mmol) and (2S,5S)-1-(tert-butoxycarbonyl)-5-methylpyrrolidine-2-carboxylic acid (2.00 g, 8.72 mmol) in acetonitrile (50 mL) was added DIEA (2.285 mL, 13.08 mmol), and the mixture was stirred at room temperature for 64 hrs. Solvent was removed in vacuo and the residue was partitioned between EtOAc (40 mL) and water (30 mL). The organic layer was washed with sat. NaHCO$_3$ and brine, dried with Na$_2$SO$_4$ and evaporated in vacuo to afford Example 4, step b (3.8 g) as yellow solid. $^1$H NMR (CDCl$_3$, 400 MHz): 7.87 (m, 1H), 7.44 (m, 2H), 5.42-5.09 (m, 2H), 4.53-4.40 (m, 1H), 4.10-3.95 (m, 1H), 2.31 (m, 2H), 2.09 (m, 1H), 1.75 (m, 1H), 1.49-1.46 (two singlet, 9H), 1.33 (m, 3H). LC/MS: Anal. Calcd. for [M+Na]$^+$ C$_{19}$H$_{24}$BrNNaO$_5$: 466.06. Found: 466.03.

EXAMPLE 4

Step c

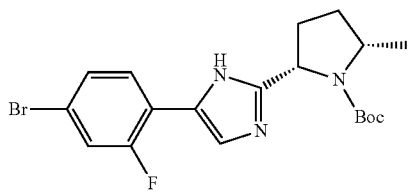 [SMILES: C[C@H]1CC[C@@H](c2ncc(-c3ccc(Br)cc3F)[nH]2)N1C(=O)OC(C)(C)C]

To a pressure tube containing a solution of Example 4, step b (3.8 g, 8.6 mmol) in xylenes (40 mL) was added ammonium acetate (6.59 g, 86 mmol), and the reaction vessel was capped and heated at 140° C. for 6 hrs. The volatile component was evaporated in vacuo and the residue was partitioned between DCM (80 mL) and water (50 mL). The organic layer was separated and washed with sat. NaHCO$_3$, and dried with Na$_2$SO$_4$. Removal of the solvent in vacuo resulted in a red oil which was purified by flash chromatograph (0-40% EtOAc/Hexane) to afford Example 4, step c (2.3 g) as brown solid. $^1$H NMR (DMSO-d$_6$, δ=2.5 ppm, 400 MHz): 7.98 (app. t, J=8.4 Hz, 1H), 7.65 (dd, J=11, 1.9 Hz, 1H), 7.45 (dd, J=8.3, 2, 1H), 7.36 (m, 1H), 4.85 (m, 1H), 3.90 (m, 1H), 2.15-2.07 (m, 3H), 1.73 (m, 1H), 1.40-1.17 (m, 12H). LC/MS: Anal. Calcd. for [M+Na]$^+$ C$_{19}$H$_{23}$$^{79}$BrFN$_3$NaO$_2$: 446.09. Found: 446.00.

EXAMPLE 4

Step d

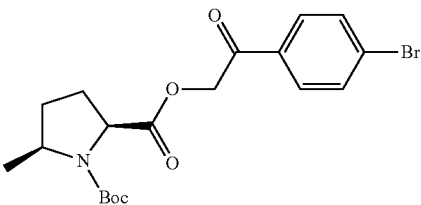 [SMILES: C[C@H]1CC[C@@H](C(=O)OCC(=O)c2ccc(Br)cc2)N1C(=O)OC(C)(C)C]

To a solution of 2-bromo-1-(4-bromophenyl)ethanone (2.425 g, 8.72 mmol) and (2S,5S)-1-(tert-butoxycarbonyl)-5-methylpyrrolidine-2-carboxylic acid (2 g, 8.72 mmol) in acetonitrile (50 mL) was added DIEA (1.524 mL, 8.72 mmol), and the mixture was stirred at room temperature for 16 hrs. Solvent was removed in vacuo and the residue was partitioned between EtOAc (40 mL) and water (30 mL). The organic phase was washed with sat. NaHCO$_3$ and brine, and dried with Na$_2$SO$_4$. Removal of the volatile component in vacuo afforded Example 4, step d (1.74 g) as light yellow solid, which was used without further purification. $^1$H NMR (DMSO-d$_6$, δ=2.5 ppm, 400 MHz): 7.95-7.90 (m, 2H), 7.81 (m, 1H), 7.79 (m, 1H), 5.63-5.44 (m, 2H), 4.36 (m, 1H), 3.99 (m, 1H), 2.27 (m, 1H), 2.09 (m, 2H), 1.63 (m, 1H), 1.41-1.37 (two singlet, 9H), 1.19 (m, 3H). LC/MS: Anal. Calcd. for [M+Na]$^+$ C$_{19}$H$_{24}$BrNNaO$_5$: 448.07. Found: 448.06.

EXAMPLE 4

Step e

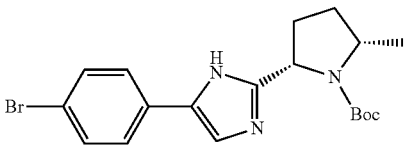

To a pressure tube containing a solution of Example 4, step d (3.4 g, 8.0 mmol) in xylenes (40 mL) was added ammonium acetate (6.15 g, 80 mmol), and the mixture was heated at 140° C. for 6 hrs. The volatile component was removed in vacuo, the residue was partitioned carefully between DCM (60 mL) and sat. NaHCO$_3$ (30 mL), and the organic layer was separated and dried with Na$_2$SO$_4$. The solvent was removed in vacuo to give red solid, which was purified by flash chromatograph (5-50% EtOAc/Hexane) to afford Example 4, step e (2.65 g) as light brown solid. $^1$H NMR (DMSO-d$_6$, δ=2.5 ppm, 400 MHz): 7.73-7.71 (m, 2H), 7.59-7.50 (m, 3H), 4.80 (m, 1H), 3.89 (m, 1H), 2.10 (m, 3H), 1.71 (m, 1H), 1.40-1.17 (m, 12H). LC/MS: Anal. Calcd. for [M+Na]$^+$ C$_{19}$H$_{24}$BrN$_3$NaO$_2$: 428.09. Found: 428.07.

EXAMPLE 4

Step f

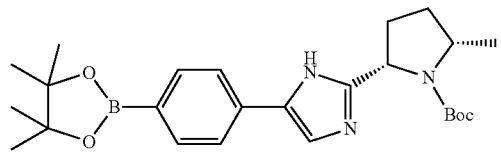

To a solution of Example 4, step e (2.64 g, 6.50 mmol) and 4,4,4',4',5,5,5',5'-octamethyl-2,2'-bi(1,3,2-dioxaborolane) (3.30 g, 13.0 mmol) in dioxane (40 mL) was added potassium acetate (1.594 g, 16.24 mmol). The mixture was degassed by bubbling nitrogen for 10 min, Pd(Ph$_3$P)$_4$ (0.375 g, 0.325 mmol) was added and degassing was continued for an additional 15 min. The reaction vessel was then sealed and heated at 80° C. for 16 hrs. The volatile component was evaporated in vacuo and the residue was partitioned between DCM (100 mL) and half sat. NaHCO$_3$ (50 mL). The organic layer was separated, dried with Na$_2$SO$_4$, and evaporated in vacuo to afford a crude red oil which was purified by flash chromatograph (10-90% EtOAc/hexanes). Example 4, step f (2.7 g) was obtained as yellow foam. $^1$H NMR (DMSO-d$_6$, δ=2.5 ppm, 400 MHz): 7.77 (d, J=8.3 Hz, 2H), 7.64-7.53 (m, 3H), 4.80 (m, 1H), 3.88 (m, 1H), 2.09 (m, 3H), 1.73 (m, 1H), 1.43-1.08 (m, 24H). LC/MS: Anal. Calcd. for [M+H]$^+$ C$_{25}$H$_{37}$BrBN$_3$O$_4$: 454.29. Found: 454.23.

EXAMPLE 4

Step g

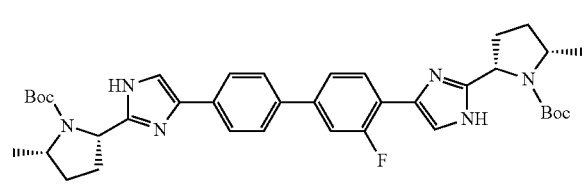

To a pressure tube containing a solution of Example 4, step f (2.70 g, 5.96 mmol) and Example 4, step c (2.30 g, 5.42 mmol) in DME (70 mL) were added water (17.50 mL) and sodium bicarbonate (2.27 g, 27.1 mmol). The mixture was degassed by bubbling nitrogen for 15 min and Pd(Ph$_3$P)$_4$ (0.313 g, 0.271 mmol) was added and degassing was continued for an additional 15 min. The reaction vessel was sealed and heated at 80° C. for 15 hrs. The solvent was evaporated in vacuo and the residue was partitioned between DCM (100 mL) and water (50 mL). The organic layer was separated, dried with Na$_2$SO$_4$ and the volatile component was removed in vacuo and the resultant red crude solid was purified by flash chromatograph (30-100% EtOAc/Hexane). Example 4, step g (1.95 g) was obtained as yellow solid. $^1$H NMR (DMSO-d$_6$, δ=2.5 ppm, 400 MHz): 8.10 (m, 1H), 7.87-7.71 (m, 4H), 7.61-7.55 (m, 3H), 7.37 (m, 1H), 4.85 (m, 2H), 3.91 (m, 2H), 2.11 (m, 6H), 1.76 (m, 2H), 1.42-1.08 (m, 24H). LC/MS: Anal. Calcd. for [M+H]$^+$ C$_{35}$H$_{48}$FN$_6$O$_4$: 671.37. Found: 671.35.

EXAMPLE 4

Step h

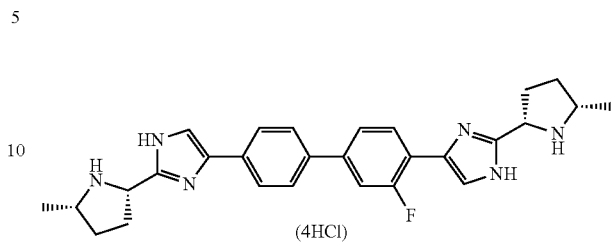

(4HCl)

To a suspension of Example 4, step g (1.95 g, 2.91 mmol) in dioxane (10 mL) was added 4N HCl in dioxane (9.72 mL, 320 mmol), and the mixture was stirred at room temperature for 6 hrs. Methanol (1 mL) was added and stirring was continued for 1 hr. The volatile component was removed in vacuo and the residue was dried under vacuum overnight. The HCl salt of Example 4, step h (1.7 g) was retrieved as yellow solid. $^1$H NMR (DMSO-d$_6$, δ=2.5 ppm, 400 MHz): 10.34/10.29/9.43/9.08 (four broad S, ~4H), 8.16 (t, J=8.3 Hz, 1H), 8.10 (br s, 1H), 8.00 (d, J=8.3 Hz, 2H), 7.92 (d, J=8.3 Hz, 2H), 7.78-7.72 (m, 3H), 4.99-4.89 (m, 2H), 3.80 (m, 2H), 2.53-2.42 (m, 4H), 2.25 (m, 2H), 1.87 (m, 2H), 1.44 (d, J=6.5, 3H), 1.43 (d, J=6.5, 3H). LC/MS: Anal. Calcd. for [M+H]$^+$ C$_{28}$H$_{32}$FN$_6$: 471.27. Found: 471.17.

EXAMPLE 4

HATU (59.4 mg, 0.156 mmol) was added to a stirred solution of (S)-2-((2R,6R)-2,6-dimethyltetrahydro-2H-pyran-4-yl)-2-((methoxycarbonyl)amino)acetic acid (Cap-2) (38.3 mg, 0.156 mmol) and the HCl salt of Example 4, step h (43.8 mg, 0.071 mmol) in DMF (0.9 mL) and DIPEA (0.10 mL, 0.57 mmol). The reaction solution was stirred at RT for 2 h and concentrated under a stream of nitrogen overnight. The residue was dissolved into MeOH (3 mL), filtered and purified by prep HPLC (Phenomenex Luna C18(2) 100×30 mm, 10 micron; MeOH/water w/TFA buffer) to afford the TFA salt of dimethyl((3-fluoro-4,4'-biphenyldiyl)bis(1H-imidazole-4,2-diyl((2S,5S)-5-methyl-2,1-pyrrolidinediyl)((1S)-1-((2R,6R)-2,6-dimethyltetrahydro-2H-pyran-4-yl)-2-oxo-2,1-ethanediyl)))biscarbamate (Example 4) (67.2 mg) as an off-white solid. $^1$H NMR (400 MHz, MeOH-d$_4$) δ 8.10-7.84 (m, 7H), 7.77-7.69 (m, 2H), 5.78-5.71 (m, 0.4H), 5.19 (td, J=10.6, 7.2 Hz, 1.6H), 4.83-4.74 (m, 2H), 4.36-4.12 (m, 4H), 3.85-3.62 (m, 8H), 2.72-1.95 (m, 10H), 1.76-1.40 (m, 10H), 1.35-1.02 (m, 14H), 0.96 (app q, J=12.2 Hz, 2H). LC-MS retention time 4.031 min; m/z 463.28 [½M+H]$^+$. LC data was recorded on a Shimadzu LC-10AS liquid chromatograph equipped with a Phenomenex-Luna 3u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 5% MeOH/95% water/10 mM ammonium acetate and solvent B was 5% water/95% MeOH/10 mM ammonium acetate. MS data was determined using a Micromass Platform for LC in electrospray mode.

EXAMPLE 5

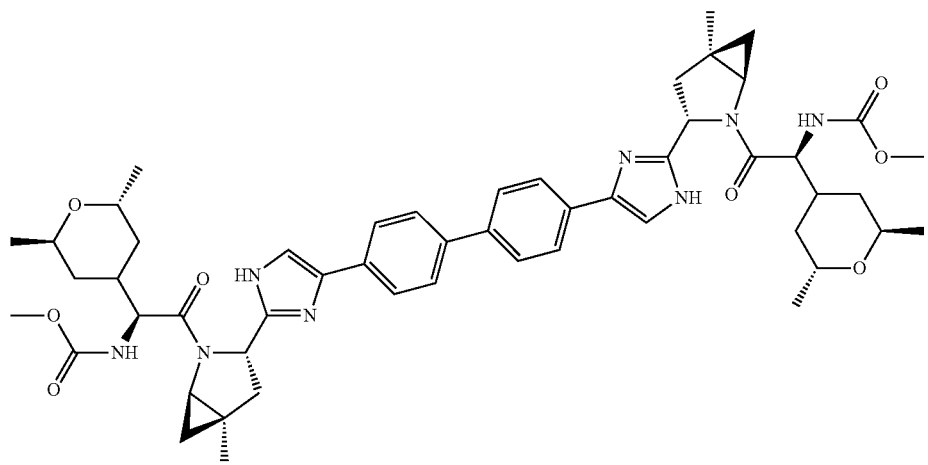

Dimethyl(4,4'-biphenyldiylbis(1H-imidazole-4,2-diyl((1R,3S,5R)-5-methyl-2-azabicyclo[3.1.0]hexane-3,2-diyl)((1S)-1-((2R,6R)-2,6-dimethyltetrahydro-2H-pyran-4-yl)-2-oxo-2,1-ethanediyl)) biscarbamate

EXAMPLE 5

Step a

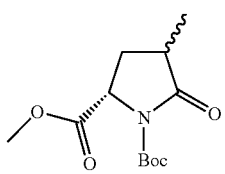 [SMILES: COC(=O)[C@@H]1CC(C)C(=O)N1C(=O)OC(C)(C)C]

The above ester was prepared as a diastereomeric mixture from (S)-1-tert-butyl 2-methyl 5-oxopyrrolidine-1,2-dicarboxylate according to the procedure described in *Tetrahedon Letters*, 2003, 3203-3205.

EXAMPLE 5

Step b

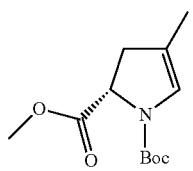

To a cooled (−50° C.) toluene (45 mL) solution of Example 5, step a (4.75 g, 18.5 mmol) was added Superhydride (19.20 mL of 1M/THF, 19.20 mmol) dropwise over 10 min. Hunig's base (13.6 mL, 78 mmol) was added, and stirred for 10 min; DMAP (0.122 g, 0.997 mmol) was added as a solid, stirred for 15 min; and, trifluoroacetic anhydride (2.98 mL, 21.1 mmol) was added dropwise over 15 min, the cooling bath was removed, and stirring was continued for 4 hr while allowing it to warm to room temperature. The reaction mixture was washed with water (50 mL), sat. NaCl (30 mL), and the organic phase was concentrated in vacuo. The resulting crude material was purified with flash chromatography (8-60% EtOAc/Hexane) to afford Example 5, step b as yellow oil (2.85 g). $^1$H NMR (CDCl$_3$, 400 MHz): 6.36 (s, 0.5H), 6.25 (s, 0.5H), 4.70-4.57 (m, 1H), 3.78 (s, 3H), 2.96 (m, 1H), 2.54 (m, 1H), 1.70 (s, 3H), 1.50 (s, 4.5H), 1.44 (s, 4.5H).

EXAMPLE 5

Step c

Example 5, step c.1

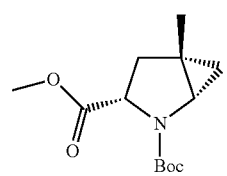

Example 5, step c.2

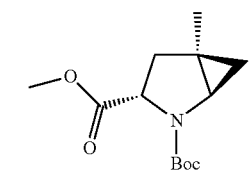

Diethylzinc (1.1 M in toluene, 59.1 mL, 65.0 mmol) was added dropwise over 20 min to a cooled (−23° C.) toluene (60 mL) solution of Example 5, step b (5.23 g, 21.7 mmol), and stirred for 10 min. Chloroiodomethane (9.44 mL, 130 mmol) was added dropwise over 10 min, and the reaction mixture was stirred at −21° C. for 16 hr. Sat. NaHCO$_3$ (60 mL) was added to the reaction mixture, the cooling bath was removed, and the mixture was stirred for 10 min. It was then filtered, and the filter cake was washed with toluene (50 mL). The filtrate was partitioned, and the organic layer was dried with Na$_2$SO$_4$, and concentrated in vacuo. The resulting crude material was purified with flash chromatography (2-10% EtOAc/Hexane) to afford Example 5, step c.1 (first elute; colorless oil; 2.88 g) and Example 5, step c.2 (second elute; colorless oil; 1.01 g). Relative stereochemical assignment was made based on NOE studies. Example 5, step c.1: $^1$H NMR (CDCl₃, 400 MHz): 4.65-4.52 (m, 1H), 3.72 (s, 3H), 3.28-3.17 (m, 1H), 2.44-2.32 (m, 1H), 2.16-2.10 (m, 1H), 1.51-1.42 (two s, 9H), 1.24 (s, 3H), 1.07 (m, 1H), 0.69-0.60 (m, 1H). Example 5, step c.2: ¹H NMR (CDCl₃, 400 MHz): 4.0 (m, 1H), 3.76 (s, 3H), 3.32-3.16 (m, 1H), 2.43 (m, 1H), 2.01 (m, 1H), 1.44 (s, 9H), 1.35 (s, 3H), 0.76-0.66 (m, 2H).

EXAMPLE 5

Step d

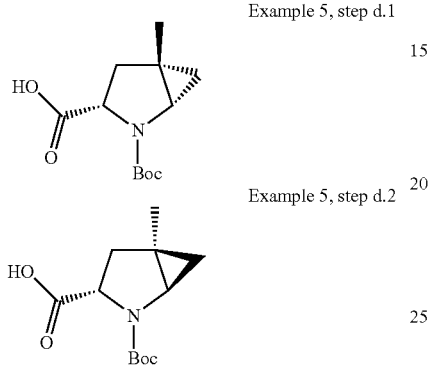

Example 5, step d.1

Example 5, step d.2

To a solution of Example 5, step c.1 (2.88 g, 11.3 mmol) in ethanol (20 mL) was added a solution of LiOH (0.324 g, 13.5 mmol) in water (10.00 mL), and the reaction mixture was stirred at room temperature for 6 hr. Most of the volatile component was removed in vacuo, and the residue was partitioned between water (20 mL) and ether (20 mL). The aqueous layer was chilled in an ice-water bath, acidified with a 1N HCl to a pH region of 2, and extracted with EtOAc (30 mL, 4×). The combined organic phase was dried with Na₂SO₄ and evaporated in vacuo to afford Example 5, step d.1 as a sticky solid (2.55 g). ¹H NMR (CDCl₃, 400 MHz): 4.64 (m, 1H), 3.25 (appt s, 1H), 2.70-2.40 (m, 1H), 2.14 (m, 1H), 1.54-1.44 (m, 9H), 1.27 (s, 3H), 1.10-0.80 (m, 1H), 0.67 (m, 1H). Example 5, step d.2 was prepared similarly from Example 5, step c.2. ¹H NMR (CDCl₃, 400 MHz): 4.13 (app br s, 1H), 3.06 (app br s, 1H), 2.55/2.41 (overlapping app br s, 2H), 1.51 (s, 9H), 1.27 (s, 3H), 0.76 (app t, J=5.6 Hz, 1H), 0.60 (app br s, 1H).

EXAMPLE 5

Step e

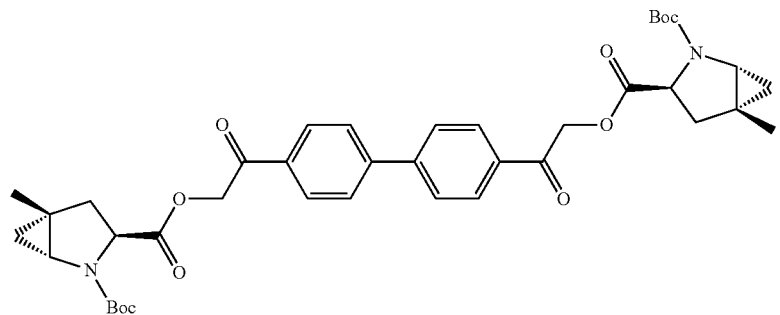 [SMILES: CC(C)(C)OC(=O)N1[C@H](C(=O)OCC(=O)c2ccc(-c3ccc(C(=O)COC(=O)[C@@H]4C[C@@]5(C)C[C@H]5N4C(=O)OC(C)(C)C)cc3)cc2)C[C@@]2(C)C[C@@H]12]

To a suspension of Example 5, step d.2 (1.09 g, 4.52 mmol) and 1,1'-(biphenyl-4,4'-diyl)bis(2-bromoethanone) (0.869 g, 2.19 mmol) in acetonitrile (40 mL) was added DIEA (0.789 mL, 4.52 mmol), and the mixture was stirred at room temperature for 4 hrs. The volatile component was removed in vacuo, and the residue was partitioned between EtOAc (70 mL) and water (50 mL). The organic layer was washed with sat. NaHCO₃ (50 mL), dried with Na₂SO₄, evaporated in vacuo and dried under vacuum to give Example 5, step e (1.54 g) as white foam. ¹H NMR (DMSO-d₆, δ=2.5 ppm, 400 MHz): 8.13 (d, J=8.3 Hz, 4H), 7.99 (d, J=8.5 Hz, 4H), 5.70-5.54 (m, 4H), 4.17 (m, 2H), 3.13-3.11 (m, 2H), 2.58-2.46 (m, 2H), 2.19 (m, 2H), 1.42-1.37 (two s, 18H), 1.24 (s, 6H), 0.76-0.70 (m, 4H). LC/MS: Anal. Calcd. for [M+Na]⁺ C₄₀H₄₈N₂NaO₁₀: 739.32. Found: 739.52.

EXAMPLE 5

Step f

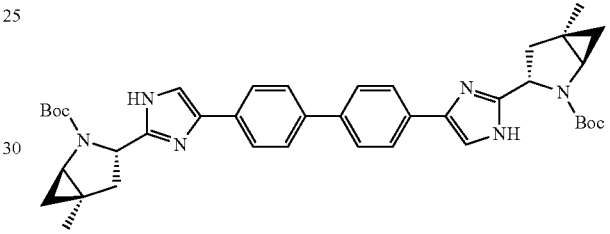

To a pressure tube containing a solution of Example 5, step e (1.54 g, 2.15 mmol) in xylenes (40 mL) was added ammonium acetate (1.656 g, 21.48 mmol), and the vessel was capped and heated at 140° C. for 5 hrs. The volatile component was removed in vacuo and the residue was carefully partitioned between DCM (50 mL) and water (50 mL) while adding sufficient saturated NaHCO₃ solution so that at the end of partitioning, the aqueous phase is neutral or basic. The organic layer was dried with Na₂SO₄, evaporated in vacuo, and the resulting crude material was purified by flash chromatograph (10-100% EtOAc/Hexane) to afford Example 5, step f (0.65 g) as brown solid. ¹H NMR (DMSO-d₆, δ=2.5 ppm, 400 MHz): 7.84-7.65 (m, 8H), 7.55-7.54 (m, 1.7H), 7.32-7.30 (m, 0.3H), 4.60 (m, 2H), 3.20 (m, 2H), 2.48-2.43 (m, 2H), 2.12 (m, 2H), 1.45-1.07 (m, 24H), 0.77 (m, 2H), 0.69 (m, 2H). LC/MS: Anal. Calcd. for [M+H]⁺ C₄₀H₄₉N₆O₄: 677.38. Found: 677.45.

EXAMPLE 5

Step g

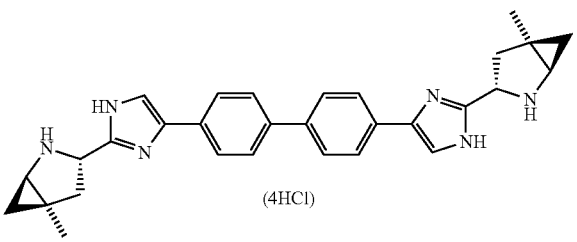

(4HCl)

To a solution of Example 5, step f (0.65 g, 0.960 mmol) in dioxane (5 mL) was added 4N HCl in dioxane (5.84 mL, 192 mmol), and the mixture was stirred at room temperature for 6 hrs. The volatile component was removed in vacuo and dried under vacuum overnight to afford the HCl salt of Example 5, step g (0.6 g) as brown solid. $^1$H NMR (DMSO-$d_6$, δ=2.5 ppm, 400 MHz): 10.5-10 (br s, ~3.2H), 7.99 (br s, 2H), 7.95 (d, J=8.5, 4H), 7.85 (d, J=8.5 Hz, 4H), 4.76 (m, 2H), 3.18 (m, 2H), 2.61-2.46 (m, 4H; overlapped with solvent signal), 1.35 (s, 6H), 1.30 (m, 2H), 0.82 (app br t, J=7.1, 2H). LC/MS: Anal. Calcd. for [M+H]$^+$ $C_{30}H_{33}N_6$: 477.28. Found: 477.22.

EXAMPLE 5

HATU (68.2 mg, 0.179 mmol) was added to a stirred solution of (S)-2-((2R,6R)-2,6-dimethyltetrahydro-2H-pyran-4-yl)-2-((methoxycarbonyl)amino)acetic acid (Cap-2) (44 mg, 0.18 mmol) and the HCl salt of Example 5, step g (50.8 mg, 0.083 mmol) in DMF (0.8 mL) and DIPEA (0.12 mL, 0.67 mmol). The reaction solution was stirred at RT for 3 h and concentrated under a stream of nitrogen overnight. The residue was dissolved into MeOH (~2.5 mL), filtered and purified by prep HPLC (Phenomenex Luna C18(2) 100×30 mm, 10 micron; MeOH/water w/11736-US-DIV TFA buffer) to afford the TFA salt of dimethyl(4,4'-biphenyldiylbis(1H-imidazole-4,2-diyl((1R,3S,5R)-5-methyl-2-azabicyclo[3.1.0]hexane-3,2-diyl)((1S)-1-((2R,6R)-2,6-dimethyltetrahydro-2H-pyran-4-yl)-2-oxo-2,1-ethanediyl)))biscarbamate (Example 5) (49.5 mg) as yellow solid. $^1$H NMR (400 MHz, MeOH-$d_4$) δ 7.93 (s, 2H), 7.90-7.82 (m, 8H), 5.02 (t, J=8.5 Hz, 2H), 4.48 (d, J=8.0 Hz, 2H), 4.26-4.18 (m, 2H), 3.80-3.71 (m, 2H), 3.68 (s, 6H), 3.60 (d, J=3.3 Hz, 2H), 2.77 (dd, J=13.4, 9.2 Hz, 2H), 2.28 (dd, J=13.1, 7.8 Hz, 4H), 1.56-1.44 (m, 6H), 1.42 (s, 6H), 1.25 (d, J=6.8 Hz, 6H), 1.09 (d, J=6.0 Hz, 6H), 1.06-0.91 (m, 6H). LC-MS retention time 3.900 min; m/z 466.29 [½M+H]$^+$. LC data was recorded on a Shimadzu LC-10AS liquid chromatograph equipped with a Phenomenex-Luna 3u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 5% MeOH/95% water/10 mM ammonium acetate and solvent B was 5% water/95% MeOH/10 mM ammonium acetate. MS data was determined using a Micromass Platform for LC in electrospray mode.

EXAMPLE 6

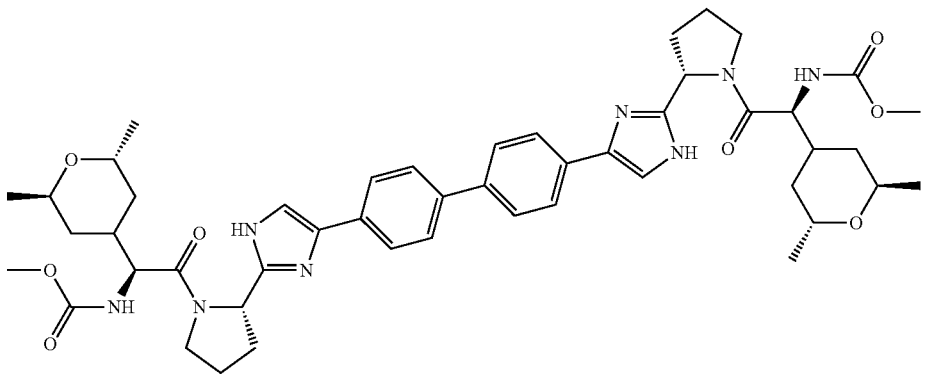

Dimethyl(4,4'-biphenyldiylbis(1H-imidazole-4,2-diyl(2S)-2,1-pyrrolidinediyl((1S)-1-((2R,6R)-2,6-dimethyltetrahydro-2H-pyran-4-yl)-2-oxo-2,1-ethanediyl))biscarbamate HATU (81 mg, 0.212 mmol) was added to a stirred solution of the HCl salt of 4,4'-bis(2-((S)-pyrrolidin-2-yl)-1H-imidazol-5-yl)-1,1'-biphenyl (prepared in WO2008/021927) (56.2 mg, 0.099 mmol) and (S)-2-((2R,6R)-2,6-dimethyltetrahydro-2H-pyran-4-yl)-2-((methoxycarbonyl)amino)acetic acid (Cap-2) (52 mg, 0.21 mmol) in DMF (1.0 mL) and DIPEA (0.14 mL, 0.79 mmol). The reaction solution was stirred at RT for 3 h and then concentrated under a stream of nitrogen. The residue was dissolved into MeOH (~5 mL), filtered and purified by prep HPLC (Phenomenex Luna C18(2) 100×30 mm, 10 micron; MeOH/water w/TFA buffer) to afford the TFA salt of dimethyl(4,4'-biphenyldiylbis(1H-imidazole-4,2-diyl(2S)-2,1-pyrrolidinediyl((1S)-1-((2R,6R)-2,6-dimethyltetrahydro-2H-pyran-4-yl)-2-oxo-2,1-ethanediyl)))biscarbamate (Example 6) (83 mg) as a light yellow solid. $^1$H NMR (400 MHz, MeOH-$d_4$) δ 7.96 (s, 2H), 7.91-7.84 (m, 8H), 5.26 (t, J=7.5 Hz, 2H), 4.24-4.09 (m, 6H), 3.93-3.84 (m, 2H), 3.74-3.68 (m, 2H), 3.67 (s, 6H), 2.63-2.55 (m, 2H), 2.39-2.12 (m, 8H), 1.57 (d, J=11.0 Hz, 2H), 1.51-1.41 (m, 2H), 1.32-1.25 (m, 2H), 1.22 (d, J=7.0 Hz, 6H), 1.05 (d, J=6.0 Hz, 6H), 0.98 (app q, J=12.3 Hz, 2H). LC-MS retention time 1.660 min; m/z 879.8 [M+H]$^+$. LC data was recorded on a Shimadzu LC-10AS liquid chromatograph equipped with a Phenomenex-Luna 3u C18 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 10% Acetonitrile/90% water/0.1% trifluoroacetic acid and solvent B was 10% water/90% Acetonitrile/0.1% trifluoroacetic acid. MS data was determined using a Micromass Platform for LC in electrospray mode.

Biological Activity

An HCV Replicon assay was utilized in the present disclosure, and was prepared, conducted and validated as described in commonly owned PCT/US2006/022197 and in O'Boyle et. al. *Antimicrob Agents Chemother.* 2005 April; 49(4):1346-53. Recommended assay methods incorporating luciferase reporters have also been used as described from commercial sources (Apath.com).

HCV-neo replicon cells and replicon cells containing resistance substitutions in the NS5A region were used to test the currently described family of compounds. The compounds were determined to have differing degrees of reduced inhibitory activity on cells containing mutations vs. the corresponding inhibitory potency against wild-type cells. Thus, the compounds of the present disclosure can be effective in inhibiting the function of the HCV NS5A protein and are understood to be as effective in combinations as previously described in application PCT/US2006/022197 and commonly owned WO/04014852. It should be understood that the compounds of the present disclosure can inhibit multiple genotypes of HCV. Table 2 shows the $EC_{50}$ (Effective 50% inhibitory concentration) values of representative compounds of the present disclosure against the HCV genotype 1b wild type, HCV genotype 1b LV/YH double resistant mutant, HCV genotype 1a, and genotype-1a YH single resistant mutant.

The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A. Compounds of the present disclosure may inhibit multiple genotypes of HCV containing multiple variants of NS5A sequences.

IV and PO Single Dose Pharmacokinetic Studies in Rat

The pharmacokinetics of Examples 1 to 6 and Compound-A (WO2008/021927) were characterized in male Sprague-Dawley rats (260-310 g) (see Table 2). In these studies, two groups of animals (N=3 per group) received compound either as an intravenous (IV) infusion (2 mg/kg over 10 minutes) via the jugular vein or by oral gavage (5 mg/kg) in a vehicle of 100% PEG 400 or 90:5:5 PEG 400:ethanol:TPGS, respectively. The rats in the oral dosing group were fasted overnight. Serial blood samples were obtained at 0.17 (IV only), 0.25, 0.5, 0.75, 1, 2, 4, 6, 8, and 24 h post dose. Blood samples (~0.3 mL) were collected from the jugular vein into $K_3$EDTA-containing tubes and then centrifuged at 4° C. (1500-2000×g) to obtain plasma. Plasma samples were stored at −20° C. until analysis by LC/MS/MS.

A bioanalytical method utilizing liquid chromatography separation followed by tandem mass spectrometry detection (LC/MS/MS) was developed for the compound analysis in rat plasma. Detection was performed using selected reaction monitoring. Ions representing the precursor $(M+H)^+$ species were selected in quadrupole 1 and collisionally dissociated with $N_2$ to generate specific product ions, which were subsequently monitored by quadrupole 3. Standard curves were prepared in male rat plasma and processed in the same manner as test samples to generate quantitative data.

Pharmacokinetic parameter values were calculated using noncompartmental methods by Kinetica. Values below the lower limit of quantification (LLOQ) were not used in calculations. Area under the curve (AUC) was calculated using the linear trapezoidal rule.

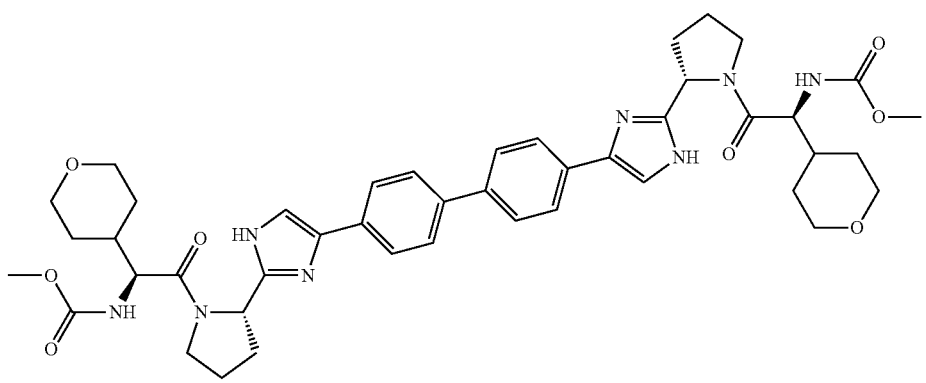

Compound-A

TABLE 2

|  | 24 h rat PK | EC50 (uM) | | | | G 1a |
| --- | --- | --- | --- | --- | --- | --- |
|  | (Auc, nM · h; oral bioavailability) | G 1b wild type | G 1b LV/YH | G 1a wild type | G 1a YH | (CC50, uM) |
| Compound-A | 103; 1.3% | 1.19E−04 | 0.020 | 5.11E−05 | 0.013 | 63.90 |
| Example-1 | 1603; 15% | 3.96E−06 | 3.19E−03 | 5.48E−06 | 9.77E−04 | 8.46 |
| Example-2 | 2219; 12% | 8.03E−06 | 1.15E−04 | 6.43E−06 | 1.58E−04 | 5.89 |
| Example-3 | 4486; 17% | 6.41E−06 | 1.91E−04 | 5.20E−06 | 1.08E−03 | 6.15 |
| Example-4 | 1729; 16% | 4.15E−06 | 4.36E−04 | 5.95E−06 | 4.02E−04 | 7.75 |
| Example-5 | 539; 6.3% | 6.85E−06 | 9.85E−06 | 3.72E−06 | 6.07E−05 | 5.34 |
| Example-6 | 1356; 5% | 3.67E−05 | 6.59E−04 | 1.62E−05 | 3.83E−04 | 15.42 |

What is claimed is:
1. A compound which is
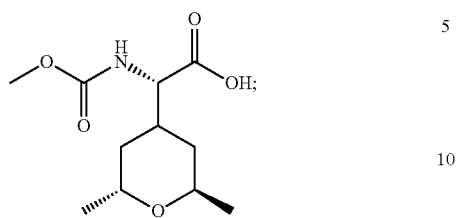
or a pharmaceutically acceptable salt thereof.
* * * * *